United States Patent
Butera et al.

(10) Patent No.: US 6,462,059 B1
(45) Date of Patent: Oct. 8, 2002

(54) 4-SUBSTITUTED-3-SUBSTITUTED-AMINO-CYCLOBUT-3-ENE-1,2-DIONES AND ANALOGS THEREOF AS NOVEL POTASSIUM CHANNEL OPENERS

(75) Inventors: John A. Butera, Clarksburg, NJ (US); Joseph R. Lennox, Morrisville; Douglas J. Jenkins, Wilmington, both of NC (US)

(73) Assignee: American Home Products, Madison, NJ (US)

( * ) Notice: Subject to any disclaimer, the term of this patent is extended or adjusted under 35 U.S.C. 154(b) by 0 days.

(21) Appl. No.: 10/095,392

(22) Filed: Mar. 12, 2002

Related U.S. Application Data

(62) Division of application No. 09/713,061, filed on Nov. 15, 2000, now Pat. No. 6,376,555, which is a continuation of application No. 09/454,051, filed on Dec. 3, 1999, now abandoned.
(60) Provisional application No. 60/135,498, filed on Dec. 4, 1998.

(51) Int. Cl.$^7$ .................. C07D 213/02; A61K 31/44
(52) U.S. Cl. ............................... 514/357; 546/334
(58) Field of Search ....................... 514/357; 546/334

(56) References Cited

U.S. PATENT DOCUMENTS

| | | | |
|---|---|---|---|
| 4,390,701 A | 6/1983 | Algieri et al. | 546/235 |
| 4,673,747 A | 6/1987 | Nohara et al. | 546/334 |
| 5,106,997 A | 4/1992 | Pu | 548/532 |
| 5,240,946 A | 8/1993 | Kinney et al. | 514/364 |
| 5,354,763 A | 10/1994 | Butera et al. | 514/352 |
| 5,397,790 A | 3/1995 | Butera et al. | 514/310 |
| 5,401,753 A | 3/1995 | Butera et al. | 514/311 |
| 5,403,853 A | 4/1995 | Butera et al | 514/415 |
| 5,403,854 A | 4/1995 | Butera et al. | 514/415 |
| 5,464,867 A | 11/1995 | Antane et al. | 514/524 |
| 5,466,712 A | 11/1995 | Butera et al. | 514/524 |
| 5,506,252 A | 4/1996 | Butera et al. | 514/399 |
| 5,512,585 A | 4/1996 | Antane et al. | 514/352 |
| 5,532,245 A | 7/1996 | Butera et al. | 514/272 |
| 5,616,802 A | 4/1997 | Nishikata et al. | 564/307 |
| 5,659,085 A | 8/1997 | Nishikata et al. | 564/307 |
| 5,763,474 A | 6/1998 | Herbst et al. | 514/399 |
| 5,811,552 A | 9/1998 | Nishikata et al. | 546/94 |

FOREIGN PATENT DOCUMENTS

| | | |
|---|---|---|
| EP | 0761643 | 4/1996 |
| JP | 7309819 | 11/1995 |
| WO | 9401436 | 1/1994 |

OTHER PUBLICATIONS

Schmidt et al., Synthesis, 579–582, 1990 (7).
English translation of Schmidt et al., Synthesis, 579–582, 1990 (7).
Liebeskind et al., J. Org. Chem., 1993, 58, 3543–3549.
Sun et al., J. Org. Chem., 1995, 60, (25) 8194–8203.
Atwal, Med. Research Reviews, vol. 12, No. 6, 569–591 (1992).
Gopalakrishnan et al., Drug Dev. Research, 28:95–127 (1993).
Primeau et al., Current Pharm. Design, 1995, I. 391–406.
Tschaen et al., Synthetic Comm., 24(6), 887–890 (1994).
Muller et al., Synthesis, pp. 50–52, 1997.
Ried et al., Liebigs Ann. Chem., 1975, 1863–1872.
Translation of Ried, et al., Liebigs Ann. Chem., 1975, 1863–1872.
Tempest et al., J. Am. Chem. Soc., 1997, 119, 7607–7608.
Thorpe, J. Chem. Soc. (B), 1968, pp. 1534–1535.
Rudy, B., Neuroscience 1988, 25, 729–749.
Saari, et al., J. Med. Chem. 1967, vol. 10, pp. 1008–1014.
Edwards, G. et al., Exp. Opin. Invest. Drugs 1996, 5 (11) 1453–1464.
Liebeskind, et al. J. Org. Chem. 1990, 55, 5359–5364.
Finkelstein, pp. 1528–1535 Ber. 1910, 43.
English translations of Finkelstein, pp. 1528–1535 Ber. 1910, 43.
Goure et al., J. Am. Chem. Soc., 1984, vol. 106, No. 21, 6417–6422.
Takai et al., J. Am. Chem. Soc., 1986, 108, 7408–7410.
Ried, Walter et al., Chem. Ber. (1969), 102(4), 1422–1430 (German).
Ried, Walter et al., Chem. Ber. (1969), 102(4), 1422–1430 (English Translation).
Ried, Walter et al., Chem. Ber. (1969), 102(4), 1431–1438 (German).
Ried, Walter et al., Chem. Ber. (1969), 102(4), 1431–1438 (Translation).
Koehler, Klaus et al, Chem. Ber. (1985), 118(5), 1903–1916 (German).
Koehler, Klaus et al, Chem. Ber.(1985), 118(5), 1903–1916 (English Translation).
International Search Report PCT/US99/28618, 1999.

*Primary Examiner*—Zinna Northington Davis
(74) *Attorney, Agent, or Firm*—Daniel B. Moran

(57) ABSTRACT

4-Substituted-3-substituted-amino-cyclobut-3-ene-1,2-diones having the Formula (I):

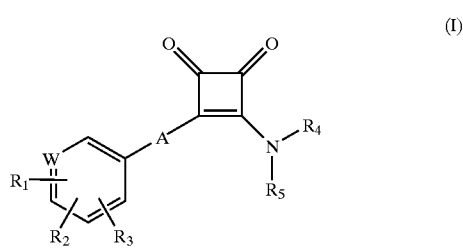

wherein $R_1$, $R_2$, $R_3$, $R_4$, $R_5$, A and W are as defined in the specification which compounds relaxes smooth muscles.

7 Claims, No Drawings

4-SUBSTITUTED-3-SUBSTITUTED-AMINO-CYCLOBUT-3-ENE-1,2-DIONES AND ANALOGS THEREOF AS NOVEL POTASSIUM CHANNEL OPENERS

CROSS REFERENCE TO RELATED APPLICATIONS

This is a divisional of application Ser. No. 09/713,061 filed on Nov. 15, 2000, now U.S. Pat. No. 6,376,555 which is a continuation of application Ser. No. 09/454,051 filed Dec. 3, 1999, now abandoned which application claims the benefit of U.S. Provisional Application No. 60/135,498, which was converted from U.S. patent application Ser. No. 09/206,012, filed Dec. 4, 1998 now abandoned pursuant to a petition filed under 37 C.F.R. 1.53(c) (2) filed Feb. 16, 1999. These applications are herein incorporated by reference in their entireties.

BACKGROUND OF INVENTION

1. Field of the Invention

The present invention relates to a novel series of 4-substituted-3-substituted-amino-cyclobut-3-ene-1,2-diones having pharmacological activity, to a process for their preparation, to pharmaceutical compositions containing them, and to their use in the treatment of disorders associated with smooth muscle contraction, via potassium channel modulation. Such disorders include, but are not limited to: urinary incontinence, asthma, premature labor, irritable bowel syndrome, congestive heart failure, angina, and cerebral vascular disease.

2. Description of the Prior Art

Modulation of potassium channels remains at the forefront of current approaches for controlling resting cell membrane potential and affecting cell excitability. A wide variety of discrete potassium channels exist and these have been thoroughly classified according to structure, function, pharmacological properties, and gating mechanisms in several recent reviews: Rudy, B. *Neuroscience* 1988, 25, 729–749; Atwal, K., *Medicinal Research Reviews* 1992, 12, 569–591; Gopalakrishnan, M. et al., *Drug Development Research* 1993, 28, 95–127; Primeau, J. et al., *Current Pharmaceutical Design* 1995, 1, 391–406; Edwards, G. et al., *Exp. Opin. Invest. Drugs* 1996, 5(11), 1453–1464. Therapeutic potential for potassium channel modulators in cardiovascular disorders, metabolic disorders, central nervous system disorders, bronchial asthma, and irritable bladder is being vastly explored.

A series of N-aryl and N-heteroaryl-1,2-diamino-cyclobutene-3,4-diones disclosed by Butera et al., in U.S. Pat. Nos. 5,354,763; 5,397,790; 5,401,753; 5,403,853; 5,403,854; 5,466,712; 5,506,252 and 5,532,245 and additionally by Antane et al., in U.S. Pat. Nos. 5,464,867 and 5,512,585 have the ability to hyperpolarize smooth muscle tissue via activation of the ATP-dependent potassium channel ($K_{ATP}$). Also disclosed is the potential utility of the N-aryl and N-heteroaryl-1,2-diaminocyclobutene-3,4-diones as useful agents for the treatment of cardiovascular disorders, metabolic disorders, central nervous system disorders, bronchial asthma, and irritable bladder.

A series of 1,2-diamino derivatives of cyclobutene-3,4-diones disclosed by Butera et al., in U.S. Pat. No. 5,763,474 have a pronounced effect on smooth muscle contractility and are useful in the treatment of urinary incontinence, irritable bladder and bowel disease, asthma, hypertension, stroke and similar diseases which are amenable to treatment with potassium channel activating compounds.

Kinney et al., in U.S. Pat. No. 5,240,946 discloses 3,4-diamino-3-cyclobutene-1,2-diones as NMDA antagonists.

Algieri et al., in U.S. Pat. No. 4,390,701 discloses 1-(substituted-amino)-2-(amino or substituted amino) cyclobutene-3,4-diones which are histamine $H_2$ antagonists useful in the treatment of peptic ulcers. Additionally, Nohara, et al., in U.S. Pat. No. 4,673,747 disclose substituted aminoalkylphenoxy derivatives which exert antagonism against histamine $H_2$ receptors.

A series of p-substituted phenyl-cyclobutenediones are reported as substrates and intermediates for monothionation reactions by Muller et al. *Synthesis* 1997,1,50–52. Related compounds are described by Schmidt et al. *Synthesis* 1990, 7,579–582 in a paper on Meerwein-arylation of semisquaric acids and semisquaric amides. Unsubstituted phenyl-cyclobutenediones are reported as reaction products between cyclobutenediones and aziridines by Ried et al. *Liebigs Ann. Chem.* 1975, 1863–1872.

In an effort to generate multiple core structure libraries by combinatorial chemistry, P. A. Tempest et al. *J. Am. Chem. Soc.* 1997, 119, 7607–7608, using Wang resin, disclose a library of p-hydroxylated phenyl-cyclobutenediones which are prepared and cleaved from the Wang resin to afford hydroxylated phenyl-cyclobutenediones.

N-Substituted-3-amino-4-phenylcyclobutenediones are reported by J. E. Thorpe *J. Chem. Soc.* (B), 1534–1535 (1968) in conjunction with proton nuclear magnetic resonance spectra studies of squaramides.

A series of p-halophenylcyclobutenediones disclosed as intermediates for the preparation of stilbene analogs which are described as having utility as non-linear optical elements with good heat and light resistance are reported in EP-0761643-A2. Additionally, Pu, in U.S. Pat. No. 5,106, 997, and Nishikata et al., in U.S. Pat. Nos. 5,616,802, 5,659,085 and 5,811,552 and in JP-A-7-309819 disclose a series of cyclobutenedione derivatives useful for the preparation of nonlinear optical elements.

A series of biphenylcyclobutenediones containing an additional heterocyclic ring as a substituent on the second phenyl ring of the bicyclic moiety and having utility as angiotensin II antagonists are reported in WO9401436-A1.

Additionally, 3-acyl-3-cyclobutene-1,2-diones are reported in several synthetic methodology papers: L. S. Liebeskind et al. *J. Org. Chem.* 1993,58(13), 3543–3549; L. Sun et al., *J. Org. Chem.* 1995, 60(25), 8194–8203.

The 4-substituted-3-distributed-amino-cyclobut-3-ene-1, 2-diones described herein are useful in the treatment of disorders associated with smooth muscle contraction, via potassium channel modulation.

SUMMARY OF THE INVENTION

Accordingly, the present invention discloses compounds represented by Formula (I):

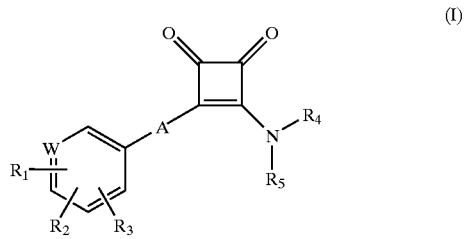

wherein:
R₁, R₂, and R₃, are, independently hydrogen, halogen, nitro, cyano, alkyl of 1 to 10 carbon atoms (optionally substituted with halogen), cycloalkyl of 3 to 10 carbon atoms, —OR₇, amino, alkylamino of 1 to 10 carbon atoms, —SO₃H, —SO₂NH₂, —SONH₂, —NHSO₂R₇,

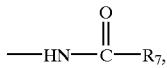

—SO₂R₇, carboxyl, aryl of 6 to 12 carbon atoms or aroyl of 7 to 12 carbon atoms;
A is a moiety selected from the group consisting of a bond, —CH₂—, —CH=CH— and —CHCOR₆;
W is selected from the group consisting of carbon and nitrogen and wherein the carbon atom may be optionally substituted with —R₁ —R₂ and —R₃.
R₄ is a alkyl of 1 to 10 carbon atoms, cycloalkyl of 3 to 10 carbon atoms, aralkyl of 7 to 20 carbon atoms, wherein the aryl group is optionally substituted with alkyl of 1 to 10 carbon atoms, nitro, halogen, cyano, —OR₇,

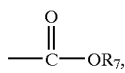

trifluoromethyl or trifluoromethoxy;
R₅ is hydrogen, alkyl of 1 to 10 carbon atoms, formyl, alkanoyl of 2 to 7 carbon atoms, alkenoyl of 3 to 7 carbon atoms,

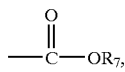

—SO₂R₇, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;
R₆ is alkyl of 1 to 10 carbon or aryl of 6 to 12 carbon atoms;
R₇ is alkyl of 1 to 10 carbon atoms (optionally substituted with halogen);
aroyl is benzoyl and naphthoyl which is optionally substituted with one to three substituents each independently selected from the group halogen, cyano, alkyl of 1 to 10 carbon atoms, alkoxy of 1 to 10 carbon atoms, —CF₃, and phenyl;
aryl is naphthyl, phenyl or phenyl optionally substituted with one to three substituents each independently selected from the group halogen, carboxy, alkyl of 1 to 10 carbon atoms, nitro, amino, alkoxy of 1 to 10 carbon atoms, and alkylamino of 1 to 10 carbon atoms;
with the following provisos that A is not a bond and W is not a carbon bearing a hydrogen;
a) when R₁ and R₂ are H; R₃ is selected from the group consisting of H, 4-methyl, 4-chloro, 4-nitro and 4-methoxy; and R₄ and R₅ are simultaneously methyl or ethyl;
b) when R₁, R₂, R₃ and R₅ are H; and R₄ is butyl;
c) when R₁, R₂ and R₅ are H; R₃ is 4-halo (chloro, bromo, fluoro, or iodo) and R₄ is alkyl of 1 to 4 carbon atoms; and
d) when R₁ is selected from the group consisting of H, 2-methyl, 2-ethyl and 2-methoxy; R₂ and R₅ are H; R₃ is 4-dimethylamino and R₄ is 2-propyl;

or pharmaceutically acceptable salts thereof.

Preferred groups of compounds of Formula (I) of this invention are those in the subgroups:

a) compounds having the general formula:

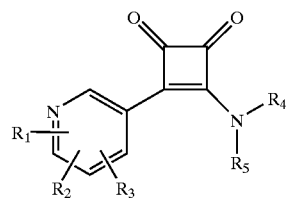

wherein R₁, R₂, R₃, R₄, and R₅ are as hereinbefore defined;

b) compounds having the general formula:

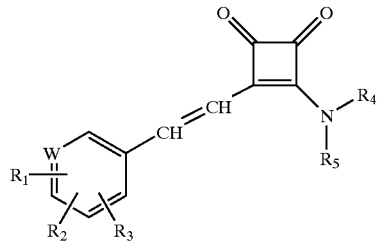

wherein R₁, R₂, R₃, R₄, and R₅ are as hereinbefore defined and W is a carbon bearing a hydrogen;

c) compounds having the general formula:

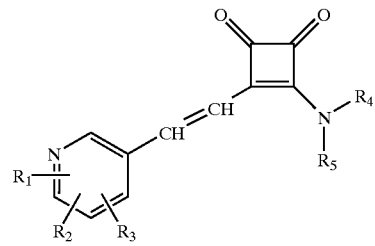

wherein R₁, R₂, R₃, R₄, and R₅ are as hereinbefore defined;

d) compounds having the general formula:

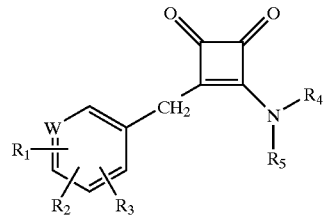

wherein R₁, R₂, R₃, R₄, and R₅ are as hereinbefore defined and W is a carbon bearing a hydrogen;

e) compounds having the general formula:

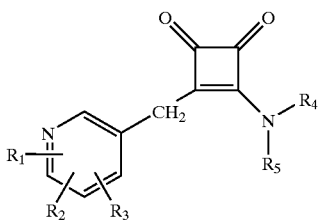

wherein $R_1$, $R_2$, $R_3$, $R_4$, and $R_5$ are as hereinbefore defined;

f) compounds having the general formula:

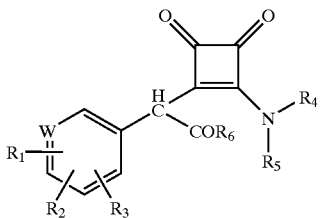

wherein $R_1$, $R_2$, $R_3$, $R_4$, $R_5$ and $R_6$ are as hereinbefore and W is a carbon bearing a hydrogen;

g) compounds having the general formula:

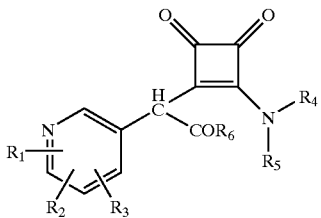

wherein $R_1$, $R_2$, $R_3$, $R_4$, $R_5$ and $R_6$ are as hereinbefore defined.

More preferred compounds of Formula (I) of this invention are those in the subgroups:

a) compounds having the general formula:

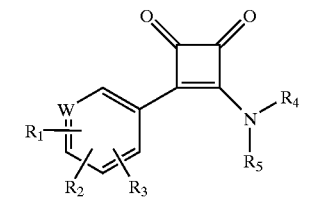

wherein:
$R_1$, $R_2$, $R_3$, $R_4$, and $R_5$ are hereinbefore defined and W is a carbon bearing a hydrogen; and b) compounds having the general formula:

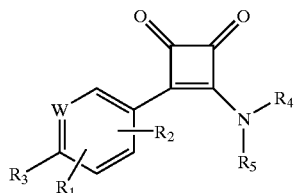

wherein:
$R_1$, $R_2$, $R_4$ and $R_5$ are hereinbefore defined, $R_3$ is alkoxy of 1 to 10 carbon atoms and W is a carbon bearing a hydrogen.

Specifically preferred compounds of this invention according to general Formula (I) are the following compounds or pharmaceutically acceptable salts thereof:

3-(1,1-Dimethyl-2-phenyl-ethylamino)-4-(4-methoxy-phenyl)-cyclobut-3-ene-1,2-dione;

3-(1,1-Dimethyl-propylamino)-4-(4-methoxy-phenyl)-cyclobut-3-ene-1,2-dione;

3-(Isopropyl-methyl-amino)-4-(4-methoxy-phenyl)-cyclobut-3-ene-1,2-dione;

3-(4-Methoxy-phenyl)-4-(1,2,2-trimethyl-propylamino)-cyclobut-3-ene-1,2-dione;

3-(4-Methoxy-phenyl)-4-[2-(3-trifluoromethyl-phenyl)-ethylamino]-cyclobut-3-ene-1,2-dione;

(−)-3-(4-Methoxy-phenyl)-1-4-((R)-1-phenyl-ethylamino)-cyclobut-3-ene-1,2-dione;

3-(4-Methoxy-phenyl)-4-(2-phenyl-propylamino)-cyclobut-3-ene-1,2-dione;

3-[2-(4-tert-Butyl-phenyl)-ethylamino]-4-(4-methoxy-phenyl)-cyclobut-3-ene-1,2-dione;

4-[3,4-Dioxo-2-(1,2,2-trimethyl-propylamino)-cyclobut-1-enyl]benzonitrile;

3-(4-Trifluoromethyl-phenyl)-4-(1,2,2-trimethyl-propylamino)-cyclobut-3-ene-1,2-dione;

4-(4-Trifluoromethyl-phenyl)-3-(1,1-dimethyl-propylamino)-cyclobut-3-ene-1,2-dione;

3-(1,1-Dimethyl-propylamino)-4-(pyridin-3-yl)-cyclobut-3-ene-1,2-dione hydrochloride;

3-[2-Oxo-1-(4-trifluoromethyl-phenyl)-propyl]-4-(1,2,2-trimethyl-propylamino)-cyclobut-3-ene-1,2-dione;

3-(4-Bromo-phenyl)-4-(1,2,2-trimethyl-propylamino)-cyclobut-3-ene-1,2-dione;

3-(4-Methoxy-benzyl)-4-(1,2,2-trimethyl-propylamino)-cyclobut-3-ene-1,2-dione one-quarter hydrate;

{2-[1-(4-Methoxy-phenyl)-2-oxo-propyl]-3,4-dioxo-cyclobut-1-enyl}-(1,2,2-trimethyl-propyl)-carbamic acid tert-butyl ester;

3-(1,1-Dimethyl-2-phenyl-ethylamino)-4-(3-methoxy-phenyl)-cyclobut-3-ene-1,2-dione;

3-[(E)-2-(4-Bromo-phenyl)-vinyl]-4-(1,2,2-trimethyl-propylamino)-cyclobut-3-ene-1,2-dione; and 4-{(E)-2-[3,4-Dioxo-2-(1,2,2-trimethyl-propylamino)-cyclobut-1-enyl]-vinyl}-benzonitrile.

In particular, this invention also provides a method of treating or inhibiting disorders associated with smooth muscle contraction, via potassium channel modulation in warm-blooded animals in need thereof, which comprises administering to said warm-blooded animals preferably mammals, most preferably humans, an effective amount of a compound of general Formula (II) or a pharmaceutically-acceptable salt thereof.

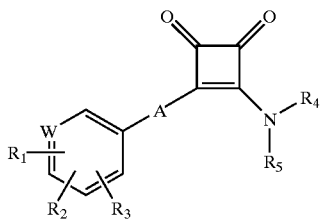

Wherein:

$R_1$, $R_2$, and $R_3$, are, independently, hydrogen, halogen, nitro, cyano, alkyl of 1 to 10 carbon atoms (optionally substituted with halogen), cycloalkyl of 3 to 10 carbon atoms, —$OR_7$, amino, alkylamino of 1 to 10 carbon atoms, —$SO_3H$, —$SO_2NH_2$, —$SONH_2$, —$NHSO_2R_7$,

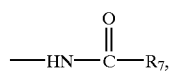

—$SO_2R_7$, carboxyl, aryl of 6 to 12 carbon atoms or aroyl of 7 to 12 carbon atoms;

A is a moiety selected from the group consisting of a bond, —$CH_2$—, —CH=CH— and —$CHCOR_6$;

W is selected from the group consisting of carbon and nitrogen and wherein the carbon atom may be optionally substituted with —$R_1$, —$R_2$ and —$R_3$;

$R_4$ is alkyl of 1 to 10 carbon atoms, cycloalkyl of 3 to 10 carbon atoms, aralkyl of 7 to 20 carbon atoms wherein the aryl group is optionally substituted with alkyl of 1 to 10 carbon atoms, nitro, halogen, cyano, —$OR_7$,

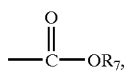

trifluoromethyl or trifluoromethoxy;

$R_5$ is hydrogen, alkyl of 1 to 10 carbon atoms, formyl, alkanoyl of 2 to 7 carbon atoms, alkenoyl of 3 to 7 carbon atoms,

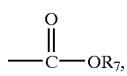

—$SO_2R_7$, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;

$R_6$ is alkyl of 1 to 10 carbon atoms, or aryl of 6 to 12 carbon atoms;

$R_7$ is alkyl of 1 to 10 carbon atoms (optionally substituted with halogen);

aroyl is benzoyl and naphthoyl which is optionally substituted with one to three substituents each independently selected from the group halogen, cyano, alkyl of 1 to 10 carbon atoms, alkoxy of 1 to 10 carbon atoms, —$CF_3$, and phenyl;

aryl is naphthyl, phenyl or phenyl optionally substituted with one to three substituents each independently selected from the group halogen, carboxy, alkyl of 1 to 10 carbon atoms, nitro, amino, alkoxy of 1 to 10 carbon atoms, and alkylamino of 1 to 10 carbon atoms; or pharmaceutically acceptable salts thereof.

Preferred groups of compounds of Formula (II) of this invention for the method of treating disorders associated with smooth muscle contraction, via potassium channel modulation including pharmaceutically acceptable salts thereof are those in the subgroups:

a) compounds having the general formula:

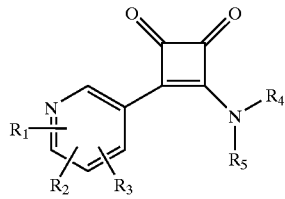

wherein $R_1$, $R_2$, $R_3$, $R_4$, and $R_5$ are as hereinbefore defined for Formula (II);

b) compounds having the general formula:

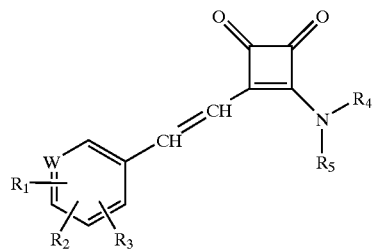

wherein $R_1$, $R_2$, $R_3$, $R_4$, and $R_5$ are as hereinbefore defined for Formula (II) and W is a carbon bearing a hydrogen;

c) compounds having the general formula:

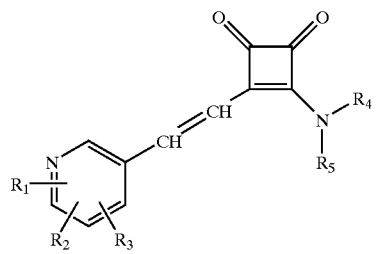

wherein $R_1$, $R_2$, $R_3$, $R_4$, and $R_5$ are as hereinbefore defined for Formula (II);

d) compounds having the general formula:

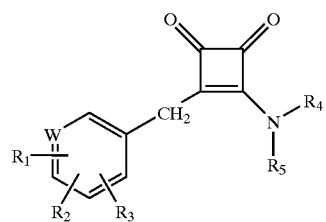

wherein $R_1$, $R_2$, $R_3$, $R_4$, and $R_5$ are as hereinbefore defined for Formula (II) and W is a carbon bearing a hydrogen;

e) compounds having the general formula:

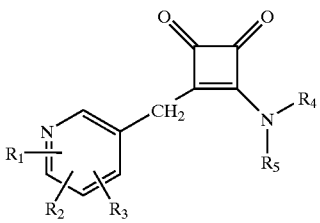

wherein $R_1$, $R_2$, $R_3$, $R_4$, and $R_5$ are as hereinbefore defined for Formula (II);

f) compounds having the general formula:

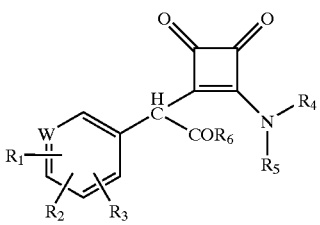

wherein $R_1$, $R_2$, $R_3$, $R_4$, $R_5$ and $R_6$ are as hereinbefore defined for Formula (II) and W is a carbon bearing a hydrogen;

g) compounds having the general formula:

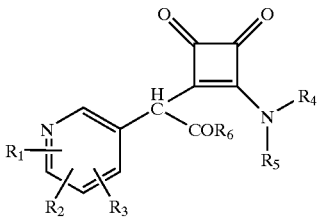

wherein $R_1$, $R_2$, $R_3$, $R_4$, $R_5$ and $R_6$ are as hereinbefore defined for Formula (II).

Preferred compounds of Formula (II) of this invention for the method of treating disorders associated with smooth muscle contraction, via potassium channel modulation including pharmaceutically acceptable salts thereof are those in the subgroups:

a) compounds having the general formula:

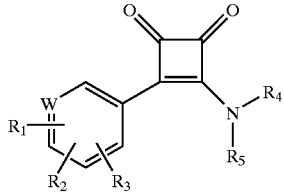

wherein:
$R_1$, $R_2$, $R_3$, $R_4$, and $R_5$ are hereinbefore defined for Formula (II) and W is a carbon bearing a hydrogen; and b) compounds having the general formula:

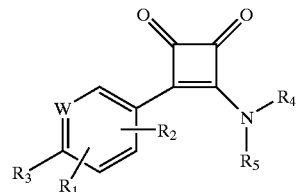

wherein:
$R_1$, $R_2$, $R_4$, and $R_5$ are hereinbefore defined for Formula (II), $R_3$ is alkoxy of 1 to 10 carbon atoms and W is a carbon bearing a hydrogen.

For the compounds of Formulae (I) and (II) defined above and referred to herein, unless otherwise noted, the following terms are defined:

Halogen, or halo as used herein means chloro, fluoro, bromo and iodo.

Alkyl as used herein means a branched or straight chain having from 1 to 10 carbon atoms and more preferably from 1 to 6 carbon atoms. Exemplary alkyl groups include methyl, ethyl, propyl, isopropyl, butyl, isobutyl, t-butyl, pentyl and hexyl.

Cycloalkyl as used herein means a saturated ring having from 3 to 10 carbon atoms and more preferably from 3 to 6 carbon atoms. Exemplary cycloalkyl rings include cyclopropyl, cyclobutyl, cyclopentyl and cyclohexyl.

Aryl as used here in means a homocyclic aromatic radical, whether or not fused, having 6 to 12 carbon atoms. Preferred adryl groups include phenyl, alpha-naphthyl and beta-naphthyl and the like optionally substituted with one to three substituents each independently selected from the group halogen, carboxy, alkyl of 1 to 10 carbon atoms, nitro, amino, alkoxy of 1 to 10 carbon atoms, and alkyl amino of 1 to 10 carbon atoms.

Aroyl as used herein refers to —C(O)aryl where aryl is as previously defined. Examples include benzoyl and naphthoyl optionally substituted with one to three substituents each independently selected from the group halogen, cyano, alkyl of 1 to 10 carbon atoms, alkoxy of 1 to 10 carbon atoms, —$CF_3$ and phenyl.

Aralkyl as used herein means an aryl-alkyl group in which the aryl and alkyl group are previously defined. Exemplary aralkyl groups include benzyl and phenethyl.

Alkenyl as used herein means a branched or straight chain having from 2 to 12 carbon atoms and more preferably from 2 to 6 carbon atoms, the chain containing at least one carbon-carbon doubles bond. Alkenyl, may be used synonymously with the term olefin and includes alkylidenes. Exemplary alkenyl groups include ethylene, propylene and isobutylene.

Alkanoyl as used herein refers to —C(O)alkyl where alkyl is as previously defined.

Alkenoyl as used herein refers to —C(O)alkenyl where alkenyl as previously defined.

Alkoxy as used herein means an —O-alkyl group in which the alkyl group is as previously described. Exemplary alkoxy groups include methoxy, ethoxy, n-propoxy, i-propoxy, n-butoxy, and t-butoxy.

Arylalkanoyl as used herein refers to a carbonyl group or radical directly bonded to an alkyl group of 1 to 10 carbon atoms which is terminally substituted by an aryl group as previously defined, for example phenylacetic acid. The aryl group is optionally substituted with one to three substituents each independently selected from the group halogen, cyano, alkyl of 1 to 10 carbon atoms, alkoxy of 1 to 10 carbon atoms, $CF_3$, and phenyl and substituted phenyl where the substituents are selected from halogen, cyano, alkyl of 1 to 10 carbon atoms, alkoxy of 1 to 10 carbon atoms and —$CF_3$.

Arylalkenoyl as used herein refers to a carbonyl group or radical directly bonded to an alkenyl group of 2 to 12 carbon atoms which is terminally substituted by an aryl group as previously defined. The aryl group is optionally substituted with one to three substituents each independently selected from the group halogen, cyano, alkyl of 1 to 10 carbon atoms, alkoxy of 1 to 10 carbon atoms, —$CF_3$, and phenyl and substituted phenyl where the substituents are selected from halogen, cyano, alkyl of 1 to 10 carbon atoms, alkoxy of 1 to 10 carbon atoms and —$CF_3$.

Arylsulfonyl as used herein refers to the radical —$SO_2$aryl where aryl is as previously defined.

Arylalkylsulfonyl as used herein refers to the radical arylalkyl$O_2$S— where arylalkyl is as previously defined.

Phenyl as used herein refers to a 6-membered aromatic ring.

Where terms are used in combination, the definition for each individual part of the combination applies unless defined otherwise. For instance, aralkyl refers to an aryl group, and alkyl refers to the alkyl group as defined above.

The range of carbon atoms defines the number of carbons in the carbon backbone and does not include carbon atoms occurring in substituent groups.

Among the specifically preferred compounds of this invention according to general Formula (II) are the specifically preferred compounds of Formula (I) or pharmaceutically acceptable salts thereof for the method of treating disorders associated with smooth muscle contraction via potassium channel modulation.

It is understood by those practicing the art that the definition of compounds of Formulae (I) and (II) when $R_1$, $R_2$, $R_3$, $R_4$, $R_5$, $R_6$ and W contain asymmetric carbons, encompass all possible stereoisomers, mixtures and regioisomers thereof which possess the activity discussed below. Such regioisomers may be obtained pure by standard separation methods known to those skilled in the art. In particular, the definition encompasses any optical isomers and diastereomers as well as the racemic and resolved enantiomerically pure R and S stereoisomers as well as other mixtures of the R and S stereoisomers and pharmaceutically acceptable salts thereof, which possess the activity discussed below. Optical isomers may be obtained in pure form by standard separation techniques or enantiomer specific synthesis. It is understood that this invention encompasses all crystalline forms of compounds of Formulae (I) and (II). The pharmaceutically acceptable salts of the basic compounds of this invention are those derived from such organic and inorganic acids as: lactic, citric, acetic, tartaric, fumaric, succinic, maleic, malonic, hydrochloric, hydrobromic, phosphoric, nitric, sulfuric, methanesulfonic and similarly known acceptable acids. Where $R_1$, $R_2$, $R_3$, $R_4$, $R_5$, or $R_6$ contains a carboxyl group, salts of the compounds in this invention may be formed with bases such as alkali metals (Na, K, Li) or alkaline earth metals (Ca or Mg).

The present invention accordingly provides a pharmaceutical composition which comprises a compound of Formula (II) of this invention in combination or association with a pharmaceutically acceptable carrier. In particular, the present invention provides a pharmaceutical composition which comprises an effective amount of a compound of this invention and a pharmaceutically acceptable carrier.

DESCRIPTION OF THE INVENTION

The compounds of the present invention may be prepared according to one or more of the general processes outlined below.

Compounds of Formulae (I) and (II), wherein A is a bond and W, $R_1$, $R_2$, $R_3$, $R_4$ and $R_5$ are hereinbefore defined may be synthesized as shown in Scheme I by the cross-coupling reaction of 3-isopropoxy-4-(tri-n-butylstannyl)-3-cyclobutene-1,2-dione 1 [J. Org. Chem. 1990, 55, 5359–5364] with an appropriate aryl halide 2 or 3-pyridylhalide (W=N), where X is a halogen and $R_1$, $R_2$ and $R_3$ are hereinbefore defined in a polar solvent such as dimethylformamide (DMF) and the like in the presence of a Pd(O) reagent such as benzylchlorobis(triphenyl-phosphine) palladium (II) and the like in the presence of cuprous iodide to give a substituted-cyclobut-3-ene-1,2-dione intermediate 3 where W and $R_1$, $R_2$ and $R_3$ are hereinbefore defined.

SCHEME I

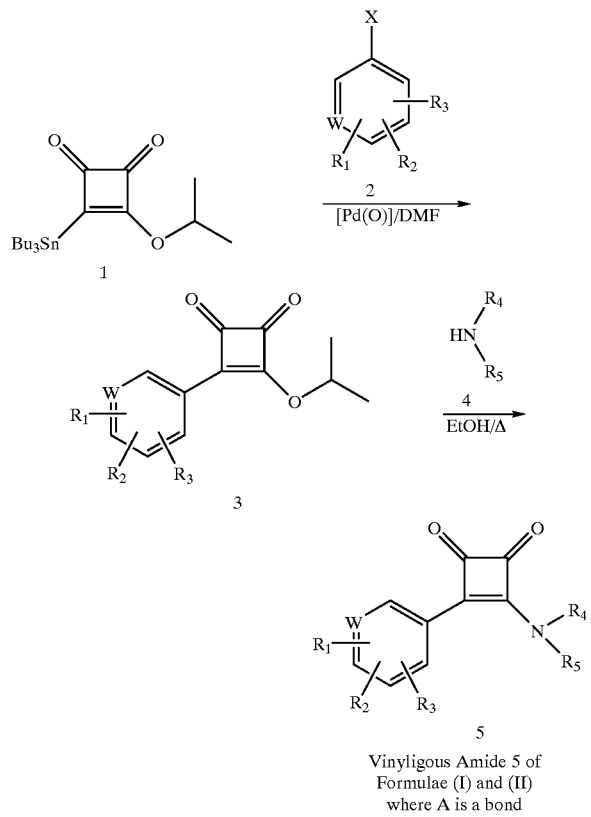

Vinyligous Amide 5 of
Formulae (I) and (II)
where A is a bond

The resulting substituted-cyclobut-3-ene-1,2-dione intermediate 3 where W and $R_1$, $R_2$ and $R_3$ are hereinbefore defined can then be converted by treatment with the appropriately substituted amine 4 where $R_4$ and $R_5$ are hereinbefore defined in a polar solvent such as ethanol and the like, forming a direct bond, to give vinyligous amide a 5 of Formulae (I) and (II) where $R_1$, $R_2$, $R_3$, $R_4$, $R_5$ and W are hereinbefore defined.

Compounds of Formulae (I) and (II) wherein A=—$CHCOR_6$ and $R_6$ is as described above may be synthesized as shown in Scheme II by reaction of ketone 6 where W, $R_1$, $R_2$, $R_3$ and $R_6$ are hereinbefore defined with diethoxysquaric acid 7 in the presence of a strong base, such as, but not limited to, potassium bis(trimethylsilyl)amide in a solvent such as tetrahydrofuran (THF) or diethyl ether and the like to give ether intermediate 8 where W, $R_1$, $R_2$, $R_3$ and $R_6$ are hereinbefore defined which could then be converted into compounds of Formulae (I) and (II) by treatment with the is appropriately substituted amine 4 in a polar solvent such as ethanol and the like to give compounds of Formulae (I) and (II) where A is a moiety —$CHCOR_6$ and W, $R_1$, $R_2$, $R_3$, $R_4$, $R_5$ and $R_6$ are hereinbefore defined.

SCHEME II

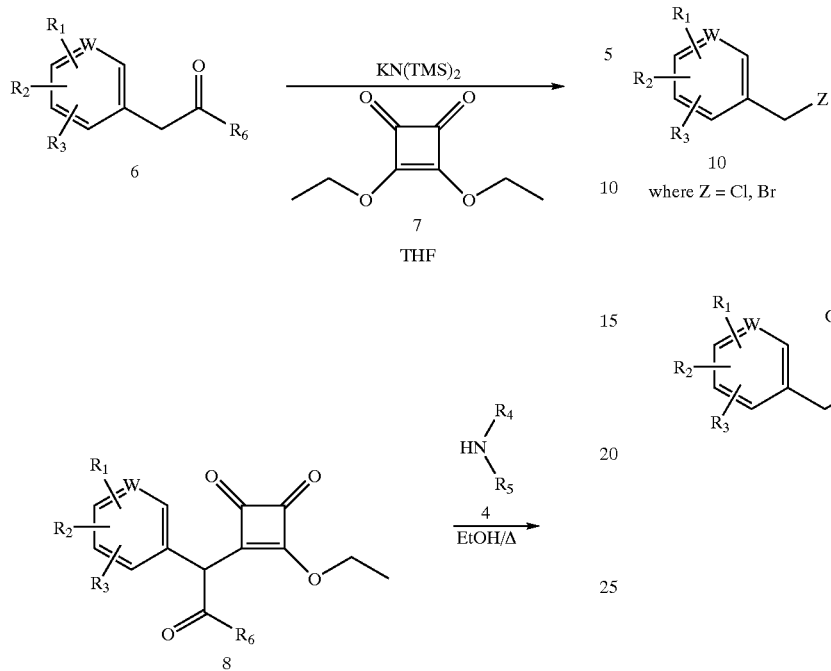

8

Formulae (I) or (II)
A = —CHCOR₆

SCHEME III

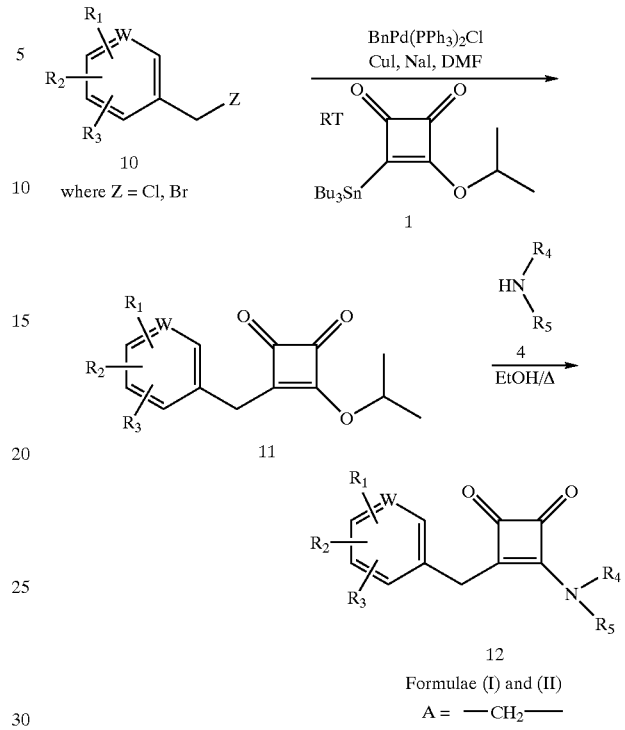

12
Formulae (I) and (II)
A = —CH₂—

Compounds of Formulae (I) and (II) wherein A is the moiety —CH₂— may be synthesized as shown in Scheme III by a transhalogenation and carbon-carbon bond forming sequence (H. Finkelstein, Ber. 1910, 43, 1528; Stille, J. K., J. Am. Chem. Soc. 1984, 106, 6417) wherein the benzylic iodide coupling partner analogous to 10 is formed in situ in the presence of cuprous iodide and concomitantly reacted with stannane 1. This procedure which is generally applicable to compounds of formula 10, wherein the group Z is either chloride or bromide, avoids the undesirable decomposition endemic to benzylic iodides to give benzyl squarate 11 where W, $R_1$, $R_2$, and $R_3$ are hereinbefore defined. Treatment of benzyl squarate 11 with substituted amine 4 where $R_4$ and $R_5$ are hereinbefore defined gives disubstituted amine squarate 12 of Formulae (I) and (II) where A is —CH₂— and where W, $R_1$, $R_2$, $R_3$, $R_4$, and $R_5$ are hereinbefore defined.

Compounds of Formulae (I) and (II) wherein A is —CH=CH— may be synthesized as shown in Scheme IV via jodomethylenation of aldehyde 13 where $R_1$, $R_2$, $R_3$ and W are hereinbefore defined, in the presence of iodoform and chrominum (II) chloride in the absence of light at room temperature(RT) and using the conditions as described by Takai, K., J. Am. Chem. Soc. 1986, 108, 7408, giving vinyl iodide 14 where $R_1$, $R_2$, $R_3$ and W are hereinbefore defined. Using the conditions as described by W. F. Goure et al, J. Am. Chem. Soc., 1984, 106, 6417, vinyl iodide 14 is reacted with stannane 1 in the presence of a Pd(O) reagent such as benzylchlorobis(triphenylphosphine) palladium (II) and the like in the presence of cuprous iodide to give styrenylcyclobutendione ethyl ester 15 where W, $R_1$, $R_2$, and $R_3$ are hereinbefore defined. Further treatment of styrenylcyclobutendione elkyl ester 15 with substituted amine 4 where $R_4$ and $R_5$ are hereinbefore defined in a polar solvent such as ethanol and the like to give disubstituted aminosquarate 16 of Formulae (I) and (II) where A is —CH=CH— and where W, $R_1$, $R_2$, $R_3$, $R_4$ and $R_5$ are hereinbefore defined.

SCHEME IV

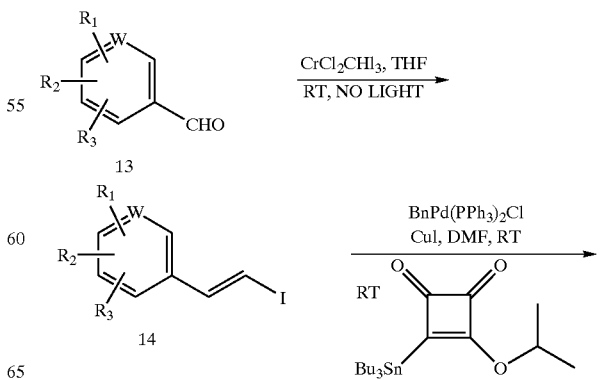

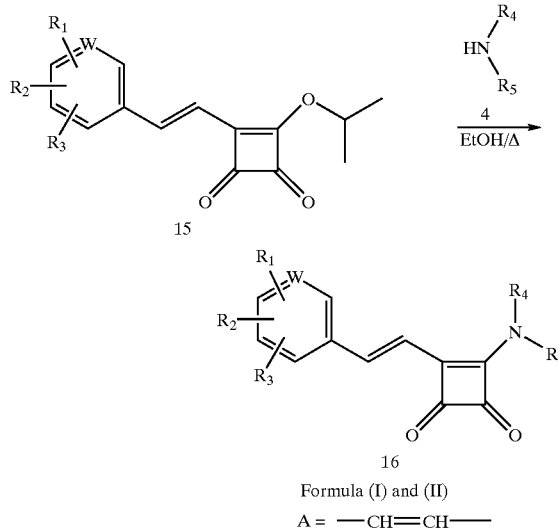

Formula (I) and (II)

A = —CH=CH—

As mentioned previously, the compounds of Formula (I) and (II) and their pharmaceutically acceptable salts have been shown in this disclosure to relax smooth muscle. They are therefore useful in the treatment of disorders associated with smooth muscle contraction, disorders involving excessive smooth muscle contraction of the urinary tract (such as incontinence) or of the gastro-intestinal tract (such as irritable bowel syndrome), asthma, and hair loss. Furthermore, the compounds of Formula (I) and (II) are active as potassium channel activators which render them useful for treatment of peripheral vascular disease, congestive heart failure, stroke, anxiety, cerebral anoxia and other neurodegenerative disorders. Moreover, compounds of Formula (I) and (II) mediate their biological effects by activating the large-conductance calcium-sensitive potassium channel ($Bk_{ca}$) or maxiK.

Compounds of the present invention are characterized by their potent smooth muscle relaxing properties in vitro. The compounds of this invention exert their smooth muscle relaxatory activity via activation of potassium channels. In addition, the compounds of the present invention are unique in that they possess intrinsic selectivity for bladder tissue over vascular tissue as demonstrated by bladder/aorta $IC_{50}$ ratios (Table 1).

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

The compositions are preferably adapted for oral administration. However, they may also be adapted for other modes of administration, for example, parenteral administration for patients suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics and β-blocking agents.

The present invention further provides a compound of the invention for use as an active therapeutic substance. Compounds of Formulae (I) and (II) are of particular use in the induction of smooth muscle relaxation.

The present invention further provides a method of treating smooth muscle disorders in mammals, including man, which comprises administering to the afflicted mammal an effective amount of a compound or a pharmaceutical composition of the invention.

The following examples are presented to illustrate rather than limit the methods for production of representative compounds of the invention.

EXAMPLE 1

3-(1,1-Dimethyl-2-Phenyl-ethylamino)-4-(4-methoxy-phenyl)-cyclobut-3-ene-1,2-dione Step 1

Preparation of 3-isopropoxy-4-(4-methoxy-phenyl)-cyclobut-3-ene-1,2-dione

To a solution of 3-isopropoxy-4-(tri-n-butyl-stannyl)-3-cyclobutene-1,2-dione (*J. Org. Chem.* 1990, 55, 5359–5364) (8.00 g, 18.65 mmol) in N,N-dimethyl-formamide (40 mL) was added 4-iodoanisole (4.85 g, 20.72 mmol). The flask was purged with nitrogen and cooled to 0° C. Benzylchloro-bis(triphenylphosphine)palladium (II) (0.942 g, 1.24 mmol) and cuprous iodide (0.355 g, 1.87 mmol) were added and the mixture was stirred at room temperature overnight. Diethylether (200 mL) was added and the mixture was washed successively with saturated aqueous ammonium chloride, 10% aqueous potassium fluoride and saturated brine. The organic phase was filtered through a plug of silica. The filtrate was dried ($MgSO_4$) and concentrated to give crude product which was dissolved in hot ethyl acetate, decolorized (charcoal) and filtered. The filtrate was treated with hexane and allowed to cool. 3-Isopropoxy-4-(4-methoxy-phenyl)-cyclobut-3-ene-1,2-dione preci-pitated as a light yellow solid (2.46 g, 54%): $^1$H NMR (DMSO-$d_6$) δ7.89(d, 2H), 7.15(d,2H), 5.45(hept, 1H), 3.82(s,3H), 1.48(d,6H).

Step 2

Preparation of 3-(1,1-Dimethyl-2-phenyl-ethylamino)-4-(4-methoxy-phenyl)-cyclobut-3-ene-1,2-dione To a solution of 3-isopropoxy-4-(4-methoxy-phenyl)-cyclobut-3-ene-1,2-dione (0.150 g, 0.609 mmol) in ethanol (3 mL) was added 1,1-dimethyl-2-phenyl-ethylamine (0.182 g, 1.22 mnol). The mixture was stirred at 70° C. overnight then filtered hot through a pad of silica gel. The filtrate was concentrated and the resulting residue was recrystallized from ethyl acetate/hexanes to give 0.170 g (83%) of the title product as a tan solid: m.p. 150–151° C.; $^1$H NMR (DMSO-$d_6$)δ8.28(s,1H), 8.00(m,2H), 7.28(m,2H), 7.26(m,1H), 7.13 (m,2H), 7.09(m,2H), 3.82(s,3H), 3.10(s,2H), 1.42(s,6H); IR (KBr) 3420, 2950, 1775, 1715, 1650, 1570, 1410, 1252, 1200, 1045, 850, 740, 700, 602, 530 $cm^{-1}$; MS (m/z) 335 [$M^+$].

Elemental analysis for $C_{21}H_{21}NO_3$: Calc'd: C,75.20; H,6.31; N,4.18. Found: C,74.35; H,6.41; N,3.90.

EXAMPLE 2

3-(1,1-Dimethyl-proylamino)-4-(4-methoxy-phenyl)-cyclobut-3-ene-1,2-dione

In a manner similar to Example 1, Step 2; 3-isopropoxy-4-(4-methoxy-phenyl)-cyclobut-3-ene-1,2-dione (0.150 g, 0.609 mmol) and tert-amyl amine (0.48 mL, 4.11 mmol) were converted to the title compound (0.14 g, 84%) m.p.: 133–135° C.; $^1$H NMR (DMSO-d$_6$) δ8.28(br s,1H), 8.04(m, 2H), 7.11(m,2H), 3.83(s,3H), 1.80(q,2H), 1.42(s,6H), 0.85 (t,3H); IR (KBr) 2980, 1765, 1725, 1600, 1423, 1310, 1260, 1175, 1030, 850 cm$^{-1}$; MS (m/z) 273 [M$^+$].

Elemental analysis for $C_{16}H_{19}NO_3$:

Calc'd: C,70.31; H,7.00; N,5.12.

Found: C,69.79; H,6.92; N,5.05.

EXAMPLE 3

3-(Isopropyl-methyl-amino)-4-(4-methoxy-phenyl)-cyclobut-3-ene-1,2-dione

In a manner similar to Example 1, Step 2; 3-isopropoxy-4-(4-methoxy-phenyl)-cyclobut-3-ene-1,2-dione (0.150 g, 0.609 mmol) and methyl-isopropylamine (0.07 mL, 0.670 mmol) in acetonitrile (3 mL) were converted to the title compound (0.10 g, 63%) m.p.: 109–115° C.; $^1$H NMR (DMSO-d$_6$) δ7.60(m,2H), 7.07(m,2H), 4.91 (m,1H), 3.81(s, 3H), 1.23(br d, 6H); MS (m/z) 259[M$^+$].

Elemental analysis for $C_{15}H_{17}NO_3$:

Calc'd: C,69.48; H,6.61; N,5.40.

Found: C,69.23; H,6.64; N,5.55.

EXAMPLE 4

3-(4-Methoxy-phenyl)-4-(1,2,2-trimethyl-propylamno)-cyclobut-3-ene-1,2-dione

In a manner similar to Example 1, Step 2; 3-isopropoxy-4-(4-methoxy-phenyl)-cyclobut-3-ene-1,2-dione (0.300 g, 1.22 mmol) and 2-amino-3,3-dimethylbutane (0.18 mL, 1.34 mmol) in acetonitrile (7 mL) were converted to the title compound (0.28 g, 80%) m.p.: 179–181° C.; $^1$H NMR (DMSO-d$_6$) δ8.56(br d,1H), 8.06(ABq,2H), 7.09(ABq,2H), 4.31(m,1H), 3.83(s,3H), 1.24(d,3H), 0.91(s,9H); IR (KBr) 3200, 2980, 1780, 1720, 1620, 1420, 1310, 1270, 1190, 1120, 1040, 840 cm$^{-1}$; MS (m/z) 287 [M$^+$].

Elemental analysis for $C_{17}H_{21}NO_3$:

Calc'd: C,71.06; H,7.37; N,4.87.

Found C,70.41; H,7.41; N,4.90.

EXAMPLE 5

3-(4-Methoxy-phenyl)-4-[2-(3-trifluoromethyl-phenyl)-ethylamino]-cyclobut-3-ene-1,2-dione In a manner similar to Example 1, Step 2; 3-isopropoxy-4-(4-methoxy-phenyl)-cyclobut-3-ene-1,2-dione (0.150 g, 0.609 mmol) and 3-trifluoromethylphenethyl-amine (0.23 g, 1.22 mmol) in ethanol (3 mL) were converted to the title compound (0.155 g, 68%) m.p. 220.2–222.3° C.; $^1$H NMR (DMSO-d6) δ9.05(br t,1H), 7.95(ABq, 2H), 7.60–7.45(m, 4H), 7.08(ABq,2H), 3.94(br t,2H), 3.83(s,3H), 3.04(t,3H); IR (KBr) 3210, 3170, 1775, 1780, 1575, 1360, 1325, 1175, 1125, 1070, 1020, 840, 800, 695 cm$^{-1}$; MS (m/z) 375 [M$^+$].

Elemental analysis for $C_{20}H_{16}NO_3F_3$:

Calc'd: C,64.00; H,4.30; N,3.73.

Found: C,64.00; H4.25; N,3.72.

EXAMPLE 6

(−)-3-(4-Methoxy-phenyl)-4-((R)-1-phenyl-ethylamlno)-cyclobut-3-ene-1,2-dione

In a manner similar to Example 1, Step 2; 3-isopropoxy-4-(4-methoxy-phenyl)-cyclobut-3-ene-1,2-dione (150 g, 0.609 mmol) and (R)-(+)-α-methyl-benzylamine (180 μL, 0.914 mmol) in ethanol (1 mL) were converted to the title compound (120 mg, 64%) m.p.: 158.7–160.1° C.; $^1$H NMR (DMSO-d$_6$) δ9.28(d,1H), 8.04(ABq,2H), 7.35(m,5H), 7.10 (ABq,2H), 3.83(s,3H), 1.64(d,3H); IR (KBr) 3260, 3060, 3030, 2970, 1770, 1720, 1600, 1560, 1520, 1440, 1410, 1380, 1340, 1310, 1260, 1220, 1180, 1120, 1100, 1025, 825, 700 cm$^{-1}$; Mg (m/z) 307 [M$^+$], $[α]^{25}_o$ −185.42° (c0.1049,THF).

Elemental analysis for $C_{19}H_{17}NO_3$:

Calc'd: C,74.25; H,5.58; N,4.56.

Found: C,73.99; H,5.56; N,4.44.

EXAMPLE 7

3(4-Methoxy-phenyl)-4-(2-phenyl-proplamino)-cyclobut-3-ene-1,2-dione

In a manner similar to Example 1, Step 2; 3-isopropoxy-4-(4-methoxy-phenyl)-cyclobut-3-ene-1,2-dione (0.150 g, 0.609 mmol) and 2-methyl-2-phenyl-ethylamine (0.165 g, 1.22 mmol) in ethanol (2 mL) were converted to the title compound (0.130 g, 66%) m.p.: 215.4–216.2° C.; $^1$H NMR (DMSO-d$_6$) δ9.07(br t,1H), 7.95(ABq,2H), 7.30–7.18(m, 5H), 7.08(ABq,2H), 3.90–3.72(m,2H), 3.82(s,3H), 3.09(m, 1H), 1.26(d,3H); IR(KBr) 3160, 2960, 1775, 1730, 1560, 1430, 1300, 1250, 1170, 1100, 1020, 840 cm$^{-1}$; MS (m/z) 322 [M+H$^+$].

Elemental analysis for $C_{20}H_{19}NO_3$: Calc'd: C, 74.75; H, 5.96; N, 4.36. Found: C, 75.06; H, 6.02; N, 4.37.

EXAMPLE 8

3-[2-(4-tert-Butyl-phenyl)-ethylamino]-4-(4-methoxy-phenyl)-cyclobut-3-ene-1,2-dione In a manner similar to Example 1, Step 2; 3-isopropoxy-4-(4-methoxy-phenyl)-cyclobut-3-ene-1,2-dione (0.150 g, 0.609 mmol) and 4-tert-butyl-phenethylamine (0.216 g, 1.22 mmol) in ethanol (2 mL) were converted to the title compound (0.180 g, 81%) m.p.: 258.1–260.2° C.; $^1$H NMR (DMSO-d$_6$) δ9.07(br t,1H), 7.97(ABq,2H), 7.29(ABq,2H), 7.14(d,2H), 7.09(d,2H), 3.87(m,2H), 3.83(s,3H), 2.84(t,2H), 1.23(s,9H); IR(KBr) 3160, 2950, 1775, 1720, 1580, 1425, 1350, 1300, 1250, 1180, 1020, 840 cm$^{-1}$; MS (m/z) 364 [M+H$^+$].

Elemental analysis for $C_{23}H_{25}NO_3$: Calc'd; C, 76.01; H, 6.93; N, 3.85. Found: C, 76.17; H, 7.01; N, 3.84.

EXAMPLE 9

4-[3,4-Dioxo-2-(1,2,2-trimethyl-propylamino)-cyclobut-1-enyl abenzonitrile

Step 1)

Preparation of 3-isopropoxy-4-(4-cyano-phenyl)-cyclobut-3-ene-1,2-dione

To a solution of 3-isopropoxy-4-(tri-n-butyl-stannyl)-3-cyclobutene-1,2-dione (6.00 g, 13.99 mmol) in N,N-dimethylformamide (20 mL) was added 4-iodobenzonitrile (3.52 g, 15.38 mmol). The flask was purged with nitrogen and cooled to 0° C.

Benzylchlorobis(triphenylphosphine)palladium (II) (0.636 g, 0.838 mmol) and cuprous iodide (0.240 g, 1.26 mmol) were added and the mixture was stirred at room temperature for 2 hours. Diethyl ether (200 mL) was added and the mixture was washed successively with saturated aqueous ammonium chloride, 10% aqueous potassium fluoride and saturated brine. The organic phase was filtered through a plug of silica. The filtrate was dried (MgSO$_4$) and concentrated to give crude product which was dissolved in hot ethyl acetate, decolorized (charcoal) and filtered. The filtrate was treated with hexane. Several crops of 3-isopropoxy-4-(4-cyano-phenyl)-cyclobut-3-ene-1,2-dione were collected. The second crop 0.27 g (7%) was of sufficient purity to take on to the next step.

Step 2

Preparation of 4-[3,4-dioxo-2-(1,2,2-trimethyl-propylamino)-cyclobut-1-enyl]-benzonitrile To a solution of 3-isopropoxy-4-(4-cyano-phenyl)-cyclobut-3-ene-1,2-dione (0.27 g, 1.12 mmol) in acetonitrile (6 mL) was added 2-amino-3,3-dimethylbutane (0.23 mL, 1.68 mmol). The mixture was stirred at room temperature overnight then filtered. The solid was recrystallized from ethyl acetate/hexanes to give 0.160 g (50%) of the title product as a white solid: m.p. 192–194° C.; $^1$H NMR (DMSO-d$_6$) δ9.01(br d,1H), 8.19(ABq,2H), 8.01(ABq,2H), 4.29(m,1H), 1.25(d,3H), 0.92 (s, 9H); IR(KBr) 3160, 2950, 2220, 1760, 1600, 1440, 1160, 1100, 850 cm$^{-1}$; MS (m/z) 282 [M$^+$].

Elemental analysis for $C_{17}H_{18}N_2O_2$: Calc'd: C, 72.32; H, 6.43; N, 9.92. Found: C, 71.20; H, 6.29; N, 9.84.

EXAMPLE 10

3-(4-Trifluoromethyl-phenyl)-4-(1,2,2-trimethyl-propylamino)-cyclobut-3-ene-1,2-dione Step 1)

Preparation of 3-isopropoxy-4-(4-trifluoro-methyl-phenyl)-cyclobut-3-ene-1,2-dione In a manner similar to example 9, Step 1, 3-isopropoxy-4-(tri-n-butylstannyl)-3-cyclobutene-1,2-dione (3.00 g, 6.99 mmol), 4-trifluoromethyl-iodobenzene (2.09 g, 7.69 mmol), benzylchlorobis(triphenylphos-phine)palladium (II) (0.318 g, 0.419 mmol) and cuprous iodide (0.12 g, 0.629 mmol) were reacted together to give 0.98 g (45%) of 3-isopropoxy-4-(4-trifluoromethyl-phenyl)-cyclobut-3-ene-1,2-dione which was of sufficient purity to use in the next step.

Step 2

Preparation of 3-(4-trifluoromethyl-phenyl)-4-(1,2,2-trimethylpropylamino)-cyclobut-3-ene-1,2-dione In a manner similar to Example 9, Step 2, 3-isopropoxy-4-(4-trifluoromethyl-phenyl)-cyclobut-3-ene-1,2-dione (0.40 g, 1.408 mmol) and 2-amino-3,3-dimethylbutane (0.28 mL, 2.11 mmol) were converted to the title compound. Recrystallization from hot ethyl acetate afforded 0.18 g (39%) of compound as a white solid: m.p. 191–193° C.; $^1$H NMR (DMSO-d$_6$) δ8.97(br d,1H), 8.22(ABq,2H), 7.88 (ABq,2H), 4.30(m,1H), 1.26(d,3H), 0.92(s,9H); IR (KBr) 3450, 3180, 2970, 1775, 1740, 1600, 1420, 1370, 1170, 1110, 1060, 850 cm$^{-1}$; MS (m/z) 325 [M$^+$].

Elemental analysis for $C_{17}H_{18}NO_2F_3$: Calc'd: C, 62.76; H, 5.58; N, 4.31. Found: C, 62.48; H, 5.60; N, 4.22.

EXAMPLE 11

4-(4-Trifluoromethyl-phenyl)-3-(1,1-dimethyl-propylamino)-cyclobut-3-ene-1,2-dione In a manner similar to Example 1, Step 2, 3-isopropoxy-4-(4-trifluoromethyl-phenyl)-cyclobut-3-ene-1,2-dione (0.30 g, 1.056 mmol) and tert-amylamine (0.86 mL, 7.39 mmol) were converted to the title compound. Recrystallization from hot ethyl acetate afforded 0.250 g (76%) of compound as a tan solkd: m.p. 115.4–119° C. (dec); $^1$H NMR (DMSO-d$_6$) δ8.60(br s,1H), 8.15(ABq, 2H), 7.86 (ABq,2H), 1.81(q,2H), 1.43(s,6H), 0.88(s,3H); IR (KBr) 3170, 2980, 1770, 1720, 1580, 1310, 1170, 1125, 1060, 1010, 850 cm$^{-1}$; MS (m/z) 311 [M$^+$].

Elemental analysis for $C_{16}H_{16}NO_2F_3$: Calc'd: C, 61.73; H5.18; N, 4.50. Found: C, 61.76; H, 4.95; N, 4.18.

EXAMPLE 12

3-(1,1-Dimethyl-propylamino)-4-(pyridin-3-yl)-cyclobut-3-ene-1,2-dione hydrochloride Step 1

Preparation of 3-isopropoxy-4-(3-pyridyl)-cyclobut-3-ene-1,2-dione

In a manner similar to Example 9, Step 1, 3-isopropoxy-4-(tri-n-butylstannyl)-3-cyclobutene-1,2-dione (1.90 g, 4.43 mmol), 3-iodopyridine (1.00 g, 4.87 mmol), benzylchlorobis (triphenylphosphine)palladium (II) (0.201 g, 0.267 mmol), and cuprous iodide (0.076 g, 0.399 mmol) were reacted together to give the title compound which was of sufficient purity to use in the next step: $^1$H NMR (DMSO-d$_6$) δ9.07 (m,1H), 8.75(m,1H), 8.20(br d,1H), 7.65(m,1H), 5.50(sept, 1H), 1.50(d,6H).

Step 2

Preparation of 3-(1,1-Dimethyl-propylamino)-4-(pyridin-3-yl)-cyclobut-3-ene-1,2-dione hydrochloride In a manner similar to Example 9, Step 2, 3-isopropoxy-4-(3-pyridyl)-cyclobut-3-ene-1,2-dione (0.20 g, 0.92 mmol) and tert-amylamine (0.75 mL, 6.45 mmol) were converted to the title compound as the free base. Treatment with ethereal HCl afforded the hydrochloride salt as a light tan solid: m.p. 152–155.9° C. (dec); $^1$H NMR (DMSO-d$_6$) δ9.20(br s,1H), 8.73(m,2H), 8.47(m,1H), 7.69(m, 1H), 4.6(br s, 1H, plus H$_2$O), 1.82(g, 2H), 1.43(s,6H), 0.88(t,3H); IR (KBr) 3475, 2970, 2470, 1050, 1770, 1590 cm$^{-1}$; MS (m/z) 244[M$^+$].

Elemental analysis for $C_{14}H_{17}N_2O_2Cl$: Calc'd: C, 59.89; H, 6.10; N, 9.98. Found: C, 58.58; H, 5.78; N, 9.57.

Examples 13–20 are prepared in a two-step procedure using the conditions described in Examples 1 or 9 using the appropriate aryl iodide, 3-isopropoxy-4-(tri-n-butylstannyi)-3-cyclobutene-1,2-dione, and the appropriate amine.

EXAMPLE 13

3-(1,1-Dimethyl-propylamino)-4-(3,4-dimethoxy-phenyl)-cyclobut-3-ene-1,2-dione

EXAMPLE 14

3-(1,1 -Dimethyl-2-phenyl-ethylamino)-4-(3,4-dimethoxy-phenyl)-cyclobut-3-ene-1,2-dione

EXAMPLE 15

3-(1,1-Dimethyl-propylamino)-4-(3-bromo-4,5-dimethoxy-phenyl)-cyclobut-3-ene-1,2-dione

EXAMPLE 16

3-(1,1-Dimethyl-2-phenyl-ethylamino)-4-(3-bromo-4,5-dimethoxy-phenyl)-cyclobut-3-ene-1,2-dione

EXAMPLE 17

3-(1,1-Dimethyl-propylamino)-4-(3-bromo-4,6-dimethoxy-phenyl)-cyclobut-3-ene-1,2-dione

EXAMPLE 18

3-(1,1-Dimethyl-2-phenyl-ethylamino)-4-(3-bromo-4,6-dimethoxy-phenyl)-cyclobut-3-ene-1,2-dione

EXAMPLE 19

3-(1,1-Dimethyl-propylamino)-4-(2-bromo-4,6-dimethoxy-phenyl)-cyclobut-3-ene-1,2-dione

EXAMPLE 20

3-(1,1-Dimethyl-2-phenyl-ethylamino)-4-(2-bromo-4,6-dimethoxy-phenyl)-cyclobut-3-ene-1,2-dione

EXAMPLE 21

3-[2-Oxo-1-(4-trifluoromethyl-phenyl)-propyl]-4-(1,2,2-trimethyl-propylamino)-cyclobut-3-ene-1,2-dione Step 1

Preparation of 3-[2-Oxo-1-(4-trifluoromethyl-phenyl)-propyl]-4-ethoxy-cyclobut-3-ene-1,2-dione A solution of 1-[(4-trifluoromethyl)phenyl]-2-propanone (*J. Med. Chem.* 1967, 10(6), 1008–14)(1.86 g, 9.208 mmol) in tetrahydrofuran (10 mL) was added dropwise (under nitrogen) to a cooled (−78° C.) solution of potassium bis (trimethyl-silyl)amide (19.3 mL; 0.5 M in toluene, 9.67 mmol) in tetrahydrofuran/diethyl ether (1:1 ratio, 80 mL). The mixture stirred at −78° C. for 15 min. and was then stirred at room temperature for 2.5 hours. The enolate solution was cooled to −78° C. and added by cannula to a cooled (−78° C.) flask containing diethyl squarate (1.50 mL, 10.13 mmol) in THF/diethyl ether (1:1 ratio, 20 mL). The reaction was stirred for 15 min. at −78° C. and was then allowed to warm to room temperature over a 1 hour period. The reaction was concentrated to give a residue which was partitioned between 0.1 N HCl and ethyl acetate. The organic phase was washed with brine, dried ($MgSO_4$) and concentrated to give crude product. Purification by flash column chromatography (2:1 hexanes/ethyl acetate) followed by trituration with petroleum ether afforded 1.18 g (39%) of title compound as a light yellow solid: $^1H$ NMR (DMSO-$d_6$) δ11.51(s,1H), 7.60(ABq,2H), 7.24(ABq,2H), 4.59(q,2H), 1.89(s,3H), 1.19(t,3H).

Step 2

Preparation of 3-[Oxo-1-(4-trifluoromethyl-phenyl)-propyl]-4-(1,1,-trimethyl-propylamino)-cyclobut-3-ene-1,2-dione 3-[2-Oxo-1-(4-trifluoromethyl phenyl)-propyl]-4-ethoxy-cyclobut-3-ene-1,2-dione (0.350 g, 1.07 mmol) and 2-amino-3,3-dimethylbutane (0.13 mL, 0.998 mmol) were stirred together in ethanol (6 mL) at room temperature overnight. Diethyl ether (25 mL) was added and the precipitated product was collected by filtration. It was stirred in diethyl ether/petroleum ether overnight, filtered and dried in vacuo to afford 0.15 g (37%) of desired product ($^1H$ NMR in $CDCl_3$ suggested the presence of both the keto and enol forms in about an 8:1 ratio) as an off-white solid: m.p. 178.2–179.8° C.; $^1H$ NMR ($CDCl_3$) δ11.74(s,1H), 7.73 (ABq,2H), 7.39(ABq,2H), 3.92(m,1H), 1.86(s,3H), 0.93(d, 3H), 0.69(s,9H); IR (KBr) 3310, 2970, 2600, 1775, 1710, 1560, 1395, 1260, 1160, 1125, 850 $cm^{-1}$; MS (m/z) 381 $[M^+]$.

Elemental analysis for $C_{20}H_{22}NO_2F_3$: Calc'd: C, 62.98; H, 5.81; N, 3.67. Found: C, 62.67.; H, 5.72; N, 3.56.

EXAMPLE 22

3-(4-Bromo-phenyl)-4-(1,2,2-trimethyl-propylamino)-cyclobut-3-ene-1,2-dione

To a heterogeneous mixture of 3-(4-bromo-phenyl)-4-isopropoxycyclobut-3-ene-1,2-dione (290 mg, 0.983 mmol) [prepared according to the method indicated in Step 1 of Example 1]in anhydrous isopropyl alcohol (6.0 mL) was added 2-amino-3,3-dimethylbutane (263 μL, 1.96 mmol) at room temperature, resulting in the formation of a yellow suspension. After 24 hours, the reaction mixture was diluted with isopropyl alcohol, filtered, washed with an excess of isopropyl alcohol, then dried under high vacuum at 65° C., affording a light yellow solid (225 mg, 68%): m.p. 210.6–211.3° C.; $^1H$ NMR (DMSO-$d_6$) δ8.81(d,1H), 8.00 ((ABq,2H), 7.75(ABq,2H), 4.29(dq,1H), 1.25(d,3H), 0.91(s, 9H); IR (KBr) 3160, 3050, 2980, 1770, 1730, 1630, 1590, 1480, 1430, 1400, 1220, 1170, 1120, 1010, 840, 810, 750, 710 $cm^{-1}$; MS (m/z) 335/337 $[M^+]$.

Elemental analysis for $C_{16}H_{18}BrNO_2$: Calc'd: C, 57.16; H, 5.40; N, 4.17. Found: C, 57.03; H, 5.34; N, 4.22.

EXAMPLE 23

3-(4-Methoxy-benzyl)-4-(1,2,2,-trimethyl-propylamino)-cyclobut-3-ene-1,2-dione one-quarter hydrate Step 1)

Preparation of 3-(4-Methoxy-benzyl)-4-isopropoxycyclobut-3-ene-1,2-dione

To a heterogeneous mixture of copper iodide (178 mg, 0.932 mmol) and sodium iodide (2.09 g, 14.0 mmol) in anhydrous N,N-dimethylformamide (5.0 mL) was added 4-methoxybenzyl chloride. The reaction mixture, which had exothermed, was stirred for 30 min. at room temperature, whereupon a solution of 3-isopropoxy-4-(tri-n-butyl-stannyl)-3-cyclobut-3-ene-1,2-dione (4.00 g, 9.32 mmol) in DMF (5.0 mL) was added, followed by addition of the benzylchlorobis(triphenylphosphine)palladium (II) catalyst (530 mg, 0.699 mmol). The yellow reaction mixture turned reddish in color and finally to a greenish black. Upon stirring at room temperature for 2 hours, the mixture was diluted with ethyl acetate (250 mL), then washed consecutively with saturated ammonium chloride (3×100 mL), 10% potassium fluoride (3×100 mL) and brine (100 mL). The organic phase was dried over $Na_2SO_4$/activated carbon and submitted to flash chromatography (elution with 40% ether-petroleum ether), affording a golden brown oil (1.04 g, 43%): $^1H$ NMR ($CDCl_3$) δ7.20(ABq,2H), 6.85(ABq,2H), 5.38(hept,1H), 3.83(s,2H), 3.79(s,3H), 1.43(d,6H).

Step 2

Preparation of 3-(4-Methoxy-benzyl)-4-(1,2,2-trimethyl-propylamino)-cyclobut-3-ene-1,2-dione one-quarter hydrate In a manner similar to Example 9, Step 2, the above indicated intermediate (350 mg, 1.34 mmol) in anhydrous isopropyl alcohol (7.0 mL) was treated with 2-amino-3,3-dimethyl-butane (272 mg, 2.69 mmol) at room temperature, affording 124 mg (31%) of the title compound ($^1H$ NMR in DMSO-$d_6$ suggested the presence of amide rotamers in a ratio of approximately 3:1): m.p. 137.4–138.1° C.; $^1H$ NMR (DMSO-$d_6$) δ8.63(d,1H), 7.16(ABq,2H), 6.87(ABq,2H), 3.90(m,1H), 3.70(s,2H), 1.15(d,3H), 0.84(s,9H); IR (KBr) 3460, 3160, 2980, 2930, 1780, 1730, 1610, 1560, 1510, 1495, 1445, 1430, 1420, 1245, 1190, 1150, 1080, 1030, 775 $cm^{-1}$; MS (m/z) 301 $[M^+]$.

Elemental analysis for $C_{18}H_{23}NO_3 \cdot 0.25 H_2O$: Calc'd: C, 70.68; H, 7.74; N, 4.58. Found: C, 70.43; H, 7.77; N, 4.55.

EXAMPLE 24

{2-[1-(4-Methoxy-phenyl)-2-oxo-propyl)]-3,4-dioxo-cyclobut-1-enyl}-(1,2,2-trimethyl-propyl)-carbamic acid tert-butyl ester Step 1

Preparation of 1-ethoxy-2-(1,2,2-trimethyl-propylamino)-cyclobut-3-ene-1,2-dione To a homogeneous solution of diethyl squarate (5.00 mL, 33.8 mmol) in anhydrous diethyl ether (250 mL) was added 2-amino-3,3-dimethylbutane (6.80 mL, 50.4 mmol) at room temperature. The resultant mixture was stirred for 1 hour, whereupon all volatiles were removed in vacuo. The residue was triturated with diethyl ether-petroleum ether, filtered and then dried under high vacuum affording 7.29 g (96%) of an off-white solid which was used without further purification.

Step 2

Preparation of 1-ethoxy-3,4-dioxo-cyclobut-1-enyl-(1,2, 2-trimethyl-propyl)-carbamic acid tert-butyl ester To a solution of the above intermediate (7.25 g, 32.2 mmol) in methylene chloride (85 mL) at room temperature was added sequentially triethylamine (4.49 mL, 32.21 mmol), di-tert-butyl dicarbonate (14.75 g, 67.6 mmol), and 4-dimethylamino-pyridine. The resultant opaque solution became yellow and homogeneous, and the ensuing reaction proceeded with gas evolution. All volatiles were removed by rotary evaporation and the residue was dried in vacuo, then submitted to flash chromatography (elution with 20% ether-petroleum ether), affording 9.63 g (93%) of a light yellow oil.

Step 3

Preparation of {2-[1-(4-Methoxy-phenyl)-2-oxo-propyl)]-3,4-dioxo-cyclobut-1-enyl}-(1,2,2-trimethyl-propyl)-carbamic acid tert-butyl ester In a manner similar to Step 1 of Example 21, was added potassium bis(trimethylsilyl)amide (2.6 mL, 1.30 mmol, 0.5 M in toluene) to a 1:1 mixture of anhydrous diethyl ether (3.5 mL) and anhydrous tetrahydrofuran (3.5 mL). The resultant mixture was cooled to −78° C., whereupon 4-methoxyphenylacetone (0.20 mL, 1.30 mmol), was added. The resultant mixture was warmed to room temperature for 2.5 hours, then cooled to −78° C. and cannula transferred to a solution of the above intermediate from Step 2(456 mg, 1.43 mmol) in diethyl ether (1.2 mL) at −78° C. Upon completed addition, the reaction mixture was warmed to room temperature, stirred for 48 hours, whereupon it was concentrated via rotary evaporation. The residue was then partitioned between methylene chloride (2×100 mL) and brine (100 mL). The combined organic phases were dried over $Mg_2SO_4$/activated carbon, filtered through a short pad of silica gel (elution with ether), concentrated, then. filtered and concentrated to give 310 mg (35%) of the hydroscopic title compound via reiterative crystallization ($^1$H NMR in DMSO-$d_6$ suggested the presence of keto-enol tautomers in a ratio of approximately 4:1): m.p. 137.4–138.1° C.; $^1$H NMR (DMSO-$d_6$) δ11.03(s,1H), 7.07(ABq,2H), 6.88(ABq, 2H), 4.65(m,1H), 3.74(s,3H), 2.03(s,3H), 1.40(br s,12H), 0.96(br s,9H); IR (KBr) 3440, 3080, 2980, 1795, 1755, 1620, 1570, 1525, 1475, 1435, 1370, 1275, 1260, 1155, 1140, 1025, 850, 800, 770 cm$^{-1}$; MS (m/z) 444 [(M+H)$^+$]/ 466 [(M+Na)$^+$].

Elemental analysis for $C_{25}H_{33}NO_6$: Calc'd: C, 67.70; H, 7.50; N, 3.16. Found: C, 66.58; H, 7.43; N, 3.07.

EXAMPLE 25

3-(1,1-Dimethyl-2-phenyl-ethylamino)-4-(3-methoxy-phenyl)-cyclobut-3-ene-1,2-dione Step 1

Preparation of 3-isopropoxy-4-(3-methoxy-phenyl)-cyclobut-3ene-1,2-dione

The title intermediate was prepared using 3-isopropoxy-4-(tri-n-butylstannyl)-3-cyclobut-3-ene-1,2-dione and 3-iodoanisole in a manner similar to the cited literature method [*J. Org. Chem.* 1990, 55, 5359–5364], providing 1.336 g (26%) of a tan solid.

Step 2

Preparation of 3-(1,1-Dimethyl-2-phenyl-ethylamino)-4-(3-methoxy-phenyl)-cyclobut-3-ene-1,2-dione In a manner similar to Step 2 of Example 9 was prepared the title compound via addition of 1,1-dimethyl-2-phenyl-ethylamnine (384 μL, 2.44 mmol) to a heterogeneous mixture of the above intermediate (300 mg, 1.22 mmol) in anhydrous ethyl alcohol (5.0 mL). Isolation followed by drying in vacuo afforded 171 mg (42%) of a white solid: m.p. 115.8–116.3° C.; $^1$H NMR (DMSO-$d_6$) δ8.47(s,1H), 7.51(m,3H), 7.08(ddd,1H), 3.81(s,3H), 1.80(q,2H), 0.86(q, 3H); IR (KBr) 3430, 3150, 2980, 2930, 1770, 1725, 1580, 1460, 1410, 1295, 1225, 1160, 1050, 1025, 875, 770 cm$^{-1}$; MS (m/z) 273 [M$^+$].

Elemental analysis for $C_{16}H_{19}NO_3$: Calc'd: C, 70.31; H, 7.01; N, 5.13. Found: C, 70.09; H, 7.05; N, 5.08.

EXAMPLE 26

3-[(E)-2-(4-Bromo-phenyl)-vinyl]-4-(1,2,2-trimethyl-propylamino)-cyclobut-3-ene-1,2-dione Step 1

Preparation of (E)-1-iodo-2-(4-bromophenyl) ethylene

To a heterogeneous mixture of chromium (II) chloride (3.98 g, 32.4 mmol) in tetrahydrofuran (40 mL) at 0° C. was added via Syringe pump over 1 hour (in the total absence of light) 4-bromo-benzaldehyde (1.00 g, 5.40 mol) and iodoform (4.25 g, 10.8 mmol) combined as a homogeneous solution in tetrahydrofuran (20 mL). The cold bath was removed, whereupon a quantitative reaction as indicated occurred within 1 hour. The reaction mixture was diluted with 1:1 ether-hexanes (200 mL) then filtered through a short pad of silica gel, concentrated to a solid tainted with residual iodoform.

Step 2

Preparation of 4-isopropoxy-3-[(E)-2-(4-bromophenyl)-vinyl]-cyclobut-3-ene-1,2-dione In a manner similar to Step 1 of Example 1 was prepared 298 mg (17%) of the title intermediate.

Step 3

Preparation of 3-[(E)-2-(4-bromophenyl)-vinyl]-4-(1,2,2-trimethyl-propylamino)-cyclobut-3-ene-1,2-dione In a manner similar to Step 2 of Example 25 was reacted the above indicated intermediate (288 mg, 0.898 mmol) and 2-amino-3,3-dimethylbutane (241 μL, 1.80 mmol) in anhydrous ethyl alcohol (3.50 mL)), affording the title compound (127 mg, 39%) as a hygroscopic yellow solid ($^1$H NMR (DMSO-$d_6$) δ8.87(d,1H), 7.71(m,5H), 7.46(d,1H), 4.02(dq, 1H), 1.19(d,3H), 0.90(s,9H); IR (KBr) 3310, 2970, 1760, 1705, 1575, 1480, 1430, 1300, 1220, 1160, 1070, 1005, 975, 875, 820, 800 cm$^{-1}$; MS (m/z) 361/363 [M$^+$].

Elemental analysis for $C_{18}H_{20}BrNO_2$: Calc'd: C, 59.68; H, 5.56;.N, 3.87. Found: C, 59.55; H, 5.38; N, 3.72.

EXAMPLE 27

4-{(E)-2-[3,4-Dioxo-2-(1,2,2-trimethyl-propylamino)-cyclobut-1-enyl]-vinyl}-benzonitrile The title compound was prepared via cyano-debrornination (Tschaen, *Synth. Comm.* 1994, 24, 887) of the title compound of Example 26. To a mixture of 3-[(E)-2-(4-bromo-phenyl)-vinyl]-4-(1,2,2-trimethyl-propylamino)-cyclobut-3-ene-1,2-dione (400 mg, 1.10 mmol) and zinc (II) cyanide (77.8 mg, 0.662 mmol) in DMF (1.20 mL) was added tetrakis(triphenylphosphine) palladium (0)(76.6 mg, 0.0662) under an atmosphere of Argon. The reaction mixture was heated to 100° C., stirred 18 hours, then worked up by dilution with toluene (150 mL), followed by consecutive extraction with ammonium hydroxide (3×50 mL) and brine (50 mL). The organic phase was further diluted with ethyl acetate (300 mL), dried over $MgSO_4$, filtered through a short pad of diatomaceous earth, and then concentrated onto silica gel. Submission to flash chromatography (multiple gradient elution with ether-petroleum ether) afforded a yellow solid which was triturated with ether-hexanes. Drying under high vacuum at 60° C. yielded the title compound (248 mg, 73%) as a hydroscopic yellow solid ($^1$H NMR in DMSO-$d_6$ suggested the presence of amide rotamers in a ratio of approximately 4:1): m.p. 240.2–241.0° C.; $^1$H NMR (DMSO-$d_6$) δ8.96(d,1H), 7.83 (m,4H), 7.64(d,1H), 7.48(d,1H), 4.03(dq,1H), 1.20(d,3H), 0.90(s,9H); IR (KBr) 3450, 3250, 3290, 2960, 1770, 1725, 1620, 1600, 1500, 1480, 1440, 1405, 1170, 1140, 1080, 980, 825, 755; MS (m/z) 309[(M+H)$^+$], 331 [(M+Na)$^+$].

Elemental analysis for $C_{19}H_{20}N_2O_2$:, Calc'd; C, 74.00; H, 6.54; N, 9.08. Found: C, 73.59; H, 6.51; N, 8.83.

The smooth muscle (bladder) relaxing activity of the compounds of this invention was established in accordance with standard pharmaceutically accepted test procedures with representative compounds as follows:

Sprague-Dawley rats (150–200 g) are rendered unconscious by $CO_2$ ashyxiation and then euthanized by cervical dislocation. The bladder is removed into warm (37° C.) physiological salt solution (PSS) of the following composition (mM): NaCl, 118.4; KCl, 4.7; $CaCl_2$, 2.5; $MgSO_4$, 4.7; $H_2O$, 1.2; $NaHCO_3$, 24.9; $KH_2PO_4$, 1.2; glucose, 11.1; EDTA, 0.023; gassed with 95% $O_2$; 2/5% $CO_2$; pH 7.4. The bladder is opened and then cut into strips 1–2 mm in width and 7–10 mm in length. The strips are subsequently suspended in a 10 mL tissue bath under an initial resting tension of 1.5 g. The strips are held in place by two surgical clips one of which is attached to a fixed hook while the other is attached to an isometric force transducer. The preparations, which usually exhibit small spontaneous contractions, are allowed to recover for a period of 1 hour prior to a challenge with 0.1 $\mu$M carbachol. The carbachol is then washed out and the tissue allowed to relax to its resting level of activity. Following a further 30 min. period of recovery an additional 15 mM KCl are introduced into the tissue bath. This increase in KCl concentration results in a large increase in the amplitude of spontaneous contractions (and initiation of contractions in previously quiescent strips) superimposed upon a small increase in basal tone. Following stabilization of this enhanced level of contractile activity, incremental increases in the concentration of test compound or vehicle are introduced into the tissue bath. Contractile activity is measured for each compound or vehicle concentration during the last minute of a 30 minute challenge.

The isometric force developed by the bladder strips is measured using a concentration required to elicit 50% inhibition of pre-drug contractile activity ($IC_{50}$ concentration) and is calculated from this concentration-response curve. The maximum percentage inhibition of contractile activity evoked by a test compound is also recorded for concentrations of test compound less than or equal to 30 $\mu$M.

The smooth muscle (aorta) relaxing activity of the compounds of this invention was established in accordance with standard pharmaceutically accepted test procedures with representative compounds as follows:

Male Sprague-Dawley rats (150–200 g) are rendered unconscious by $CO_2$ asphyxiation and then euthanized by cervical dislocation. The thoracic aorta is removed into warm (37 deg.C.) physiological salt solution (PSS) of the following composition (mM)Nacl, 118.4; KCl, 4.7; $CaCl_2$, 2.5; $MgSO_4 \cdot 7H_2O$, 1.2; $NaHCO_3$, 24.9; $KH_2PO_4$, 1,2; glucose, 11.1; EDTA, 0.023; gassed with 95% $O_2$/5% $CO_2$; pH 7.4. The aorta is cleaned of fat and loose adventitia and cut into rings 3–4 mm in width. The rings are subsequently suspended between two stainless steel wire tissue holders in a 10 ml tissue bath. One wire tissue holder is attached to a fixed hook while the other is attached to an isometric force transducer. Resting tension is set at 1 g. The tissues are to recover for a period of 60 mins. prior to beginning the experiment. Tissues are challenged with PSS containing 25 mM KCl to elicit a contracture. The tissues are then washed repeatedly with fresh PSS over a period of mins. and allowed to recover to baseline tension. PSS containing 30–35 mM KCl is then introduced into the tissue bath to evoke a contracture that is allowed to stabilize for not less than 45 minutes. (Other stimuli such as norepine-phrine, PGF2a, histamine, angiotensin II, endothelin or PSS containing 80 mM KCl may also be used to evoke a contracture as necessary). Increasing concentrations of test compound or vehicle are then added to the tissue bath in a cumulative fashion.

Isometric force development by the aortic rings is measured using a force transducer and recorded on a polygraph.

The percentage inhibition of contractile force evoked by each concentration of a given test compound is used to generate a concentration-response curve. The concentration of test compound required to elicit 50% inhibition of pre-drug contractile force ($IC_{50}$ concentration) is calculated from this dose-response curve. [Log concentration versus response curves are approximately linear between 20% and 80% of the maximum response. As such, the $IC_{50}$ concentration of the drug is determined by linear regression analysis (where x=log concentration and y=% inhibition) of the data points in the 20% to 80% region of the curve]. The maximum percentage inhibition of contractile force evoked by a test compound is also recorded for concentrations of test compound < or = to 30 $\mu$M. Data collected from 2 animals are averaged for primary screens.

The results of these studies are shown in Table I.

TABLE I

| Ex. No. | n | Bladder Tissue $IC_{50}$ ($\mu$M) | n | Aorta Tissue $IC_{50}$ ($\mu$M) | Ratio Aorta $IC_{50}$ Bladder $IC_{50}$ |
|---|---|---|---|---|---|
| 1 | 2 | 1.2 ± 0.26 | 2 | 3.25 ± 0.35 | 2.71 |
| 2 | 4 | 2.5 ± 0.49 | 2 | 37.65 ± 6.05 | 15.1 |
| 3 | 4 | 11.99 ± 2.4 | 3 | 46.2 ± 7.8 | 3.85 |
| 4 | 4 | 9.51 ± 1.8 | 5 | 24.2 ± 6.3 | 2.56 |
| 5 | 4 | 1 = 9.75 ± 4.4%* | | — | — |
| 6 | 2 | 26.9 ± 0.3 | | — | — |
| 7 | 2 | 1 = 7.4 ± 5.7% | | — | — |
| 8 | 1 | 11.2 | | — | — |
| 9 | 3 | 1 = 27.2 ± 8.6% | | — | — |
| 10 | 2 | 15.6 ± 3.7 | | — | — |
| 11 | 2 | 1 = 34.2 ± 6.0% | | — | — |
| 12 | 2 | 1 = 26.0 ± 2.2% | | — | — |
| 21 | 3 | 16.2 ± 6.82 | | — | — |
| 22 | 3 | 25.7 ± 1.1 | | — | — |
| 23 | 2 | 1 = 10.2 ± 5.6% | | — | — |
| 24 | 1 | 15.9 | | — | — |
| 25 | 2 | 1 = 30.35 ± 0.52%* | | — | — |
| 26 | 3 | 15.6 ± 8%* | | — | — |
| 27 | 5 | 2.94 ± 0.62 | | — | — |

*Percent inhibition at 30 $\mu$M

Hence, the compounds of this invention are selective for bladder tissue and have a pronounced effect on smooth muscle contractility and are useful in the treatment of urinary incontinence, irritable bladder and bowel disease, asthma, stroke, and similar diseases as mentioned above, which are amenable to treatment with potassium channel activating compounds by administration, orally, parenterally, or by aspiration to a patient in need thereof.

What is claimed is:

1. A compound having the Formula (I):

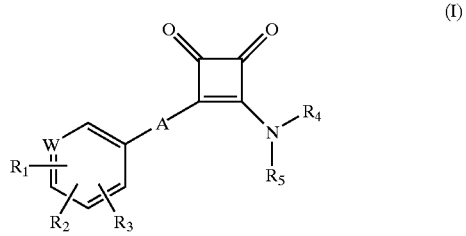

wherein:

$R_1$, $R_2$, and $R_3$, are, independently, hydrogen; halogen; nitro; cyano; alkyl of 1 to 10 carbon atoms optionally substituted with halogen; cycloalkyl of 3 to 10 carbon atoms; —$OR_7$; amino; alkylamino of 1 to 10 carbon atoms; —$SO_3H$; —$SO_2NH_2$; —$SONH_2$; —$NHSO_2R_7$;

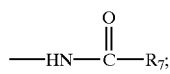

—SO₂R₇; carboxyl; aryl of 6 to 12 carbon atoms optionally substituted with one to three substituents each independently selected from the group halogen, carboxy, alkyl of 1 to 10 carbon atoms, nitro, amino, alkoxy of 1 to 10 carbon atoms, and alkyl amino of 1 to 10 carbon atoms; or aroyl of 7 to 12 carbon atoms optionally substituted with one to three substituents each independently selected from the group halogen, cyano, alkyl of 1 to 10 carbon atoms, alkoxy of 1 to 10 carbon atoms, —CF₃ and phenyl;

A is a bond;

W is nitrogen;

R₄ is a alkyl of 1 to 10 carbon atoms; cycloalkyl of 3 to 10 carbon atoms; aralkyl of 7 to 20 carbon atoms; wherein the aryl group of the aralkyl group of R₄ is optionally substituted with alkyl of 1 to 10 carbon atoms, nitro, halogen cyano, —OR₇,

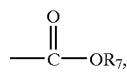

trifluoromethyl or trifluoromethoxy;

R₅ is hydrogen; alkyl of 1 to 10 carbon atoms; formyl; alkanoyl of 2 to 7 carbon atoms; alkenoyl of 3 to 7 carbon atoms;

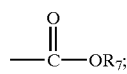

—SO₂R₇; aroyl of 7 to 12 carbon atoms optionally substituted with one to three substituents each independently selected from the group halogen, cyano, alkyl of 1 to 10 carbon atoms, alkoxy of 1 to 10 carbon atoms, —CF₃ and phenyl; arylalkenoyl of 9 to 20 carbon atoms wherein the aryl group is optionally substituted with one to three substituents each independently selected from the group halogen, cyano, alkyl of 1 to 10 carbon atoms, alkoxy of 1 to 10 carbon atoms, CF₃, and phenyl and substituted phenyl where the substituents are selected from halogen, cyano, alkyl of 1 to 10 carbon atoms, alkoxy of 1 to 10 carbon atoms and —CF₃; arylsulfonyl of 6 to 12 carbon atoms wherein the aryl group is optionally substituted with one to three substituents each independently selected from the group halogen, carboxy, alkyl of 1 to 10 carbon atoms, nitro, amino, alkoxy of 1 to 10 carbon atoms, and alkyl amino of 1 to 10 carbon atoms; arylalkanoyl of 8 to 12 carbon atoms wherein the aryl group is optionally substituted with one to three substituents each independently selected from the group halogen, cyano, alkyl of 1 to 10 carbon atoms, alkoxy of 1 to 10 carbon atoms, CF₃, and phenyl and substituted phenyl where the substituents are selected from halogen, cyano, alkyl of 1 to 10 carbon atoms, alkoxy of 1 to 10 carbon atoms and —CF₃; or arylalkylsulfonyl of 7 to 12 carbon atoms wherein the aryl group is optionally substituted with one to three substituents each independently selected from the group halogen, carboxy, alkyl of 1 to 10 carbon atoms, nitro, amino, alkoxy of 1 to 10carbon atoms, and alkyl amino of 1 to 10 carbon atoms;

R₆ is alkyl of 1 to 10 carbon atoms; or aryl of 6 to 12 carbon atoms wherein the aryl group is optionally substituted with one to three substituents each independently selected from the group halogen, carboxy, alkyl of 1 to 10 carbon atoms, nitro, amino, alkoxy of 1 to 10 carbon atoms, and alkyl amino of 1 to 10 carbon atoms;

R₇ is a alkyl of 1 to 10 carbon atoms optionally substituted with halogen;

Aryl means a homocyclic aromatic radical, whether or not fused, having 6 to 12 carbon atoms optionally substituted with one to three substituents;

Aroyl of 7 to 12 carbon atoms refers to —C(O)aryl;

or pharmaceutically acceptable salts thereof.

2. A compound according to claim 1 wherein A is a bond and W is nitrogen or a pharmaceutically acceptable salt thereof.

3. The compound of claim 1 which is 3-(1,1-dimethylpropylamino)-4-(pyridin-3-yl)-cyclobut-3-ene-1,2-dione hydrochloride or a pharmaceutically acceptable salt thereof.

4. A pharmaceutical composition for treating or inhibiting disorders associated with smooth muscle contraction, via potassium channel modulation in warm-blooded animals in need thereof, which comprises administering to said warm-blooded animals, an effective amount of a compound of Formula (II)

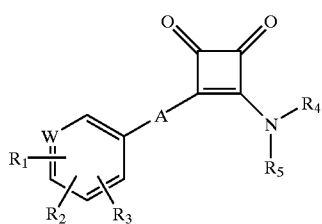

(II)

wherein:

R₁, R₂, and R₃, are, independently, hydrogen; halogen; nitro; cyano; alkyl of 1 to 10 carbon atoms (optionally substituted with halogen); cycloalkyl of 3 to 10 carbon atoms; —OR₇; amino; alkylamino of 1 to 10 carbon atoms; —SO₃H; —SO₂NH₂; —SONH₂; —NHSO₂R₇;

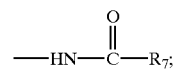

—SO₂R₇; carboxyl; aryl of 6 to 12 carbon atoms optionally substituted with one to three substituents each independently selected from the group halogen, carboxy, alkyl of 1 to 10 carbon atoms, nitro, amino, alkoxy of 1 to 10 carbon atoms, and alkyl armino of 1 to 10 carbon atoms; or aroyl of 7 to 12 carbon atoms optionally substituted with one to three substituents each independently selected from the group halogen, cyano, alkyl of 1 to 10 carbon atoms, alkoxy of 1 to 10 carbon atoms, —CF₃ and phenyl;

A is a bond;

W is nitrogen;

R₄ is a alkyl of 1 to 10 carbon atoms; cycloalkyl of 3 to 10 carbon atoms; aralkyl of 7 to 20 carbon atoms, wherein the aryl group of the aralkyl group of R₄ is optionally substituted with alkyl of 1 to 10 carbon atoms, nitro, halogen cyano, —OR₇,

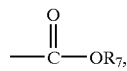

trifluoromethyl or trifluoromethoxy;

R$_5$ is hydrogen; alkyl of 1 to 10 carbon atoms; formyl; alkanoyl of 2 to 7 carbon atoms; alkenoyl of 3 to 7 carbon atoms;

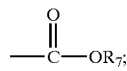

—SO$_2$R$_7$; aroyl of 7 to 12 carbon atoms optionally substituted with one to three substituents each independently selected from the group halogen, cyano, alkyl of 1 to 10 carbon atoms, alkoxy of 1 to 10 carbon atoms, —CF$_3$ and phenyl; arylalkenoyl of 9 to 20 carbon atoms wherein the aryl group is optionally substituted with one to three substituents each independently selected from the group halogen, cyano, alkyl of 1 to, 10 carbon atoms, alkoxy of 1 to 10 carbon atoms, CF$_3$, and phenyl and substituted phenyl where the substituents are selected from halogen, cyano, alkyl of 1 to 10 carbon atoms, alkoxy of 1 to 10 carbon atoms and —CF$_3$; arylsulfonyl of 6 to 12 carbon atoms wherein the aryl group is optionally substituted with one to three substituents each independently selected from the group halogen, carboxy, alkyl of 1 to 10 carbon atoms, nitro, amino, alkoxy of 1 to 10 carbon atoms, and alkyl amino of 1 to 10 carbon atoms; arylalkanoyl of 8 to 12 carbon atoms wherein the aryl group is optionally substituted with one to three substituents each independently selected from the group halogen, cyano, alkyl of 1 to 10 carbon atoms, alkoxy of 1 to 10 carbon atoms, CF$_3$, and phenyl and substituted phenyl where the substituents are selected from halogen, cyano, alkyl of 1 to 10 carbon atoms, alkoxy of 1 to 10 carbon atoms and —CF$_3$; or arylalkylsulfonyl of 7 to 12 carbon atoms wherein the aryl group is optionally substituted with one to three substituents each independently selected from the group halogen, carboxy, alkyl of 1 to 10 carbon atoms, nitro, amino, alkoxy of 1 to 10 carbon atoms, and alkyl amino of 1 to 10 carbon atoms;

R$_6$ is alkyl of 1 to 10 carbon atoms; or aryl of 6 to 12 carbon atoms wherein the aryl group is optionally substituted with one to three substituents each independently selected from the group halogen, carboxy, alkyl of 1 to 10 carbon atoms, nitro, amino, alkoxy of 1 to 10 carbon atoms, and alkyl amino of 1 to 10 carbon atoms;

R$_7$ is a alkyl of 1 to 10 carbon atoms optionally substituted with halogen;

Aryl means a homocyclic aromatic radical, whether or not fused, having 6 to 12 carbon atoms optionally substituted with one to three substituents;

Aroyl of 7 to 12 carbon atoms refers to —C(O)aryl;

or a pharmaceutically acceptable, salt thereof and one or more pharmaceutically acceptable carriers or excipients.

5. A method of treating or inhibiting disorders associated with smooth muscle contraction, via potassium channel modulation in warm-blooded animals in need thereof, which comprises administering to said warm-blooded animals, an effective amount of a pharmaceutical composition of claim 4 or a compound of Formula (II):

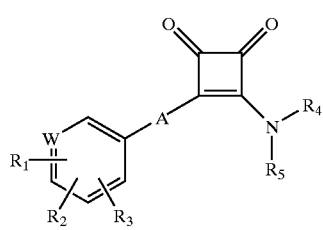

wherein:

R$_1$, R$_2$, and R$_3$, are, independently, hydrogen; halogen; nitro; cyano; alkyl of 1 to 10 carbon atoms (optionally substituted with halogen); cycloalkyl of 3 to 10 carbon atoms; —OR$_7$; amino; alkylamino of 1 to 10 carbon atoms; —SO$_3$H; —SO$_2$NH$_2$; —SONH$_2$; —NHSO$_2$R$_7$;

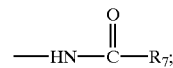

—SO$_2$R$_7$; carboxyl; aryl of 6 to 12 carbon atoms optionally substituted with one to three substituents each independently selected from the group halogen, carboxy, alkyl of 1 to 10 carbon atoms, nitro, amino, alkoxy of 1 to 10 carbon atoms, and alkyl amino of 1 to 10 carbon atoms; or aroyl of 7 to 12 carbon atoms optionally substituted with one to three substituents each independently selected from the group halogen, cyano, alkyl of 1 to 10 carbon atoms, alkoxy of 1 to 10 carbon atoms, —CF$_3$ and phenyl;

A is a bond;

W is nitrogen;

R$_4$ is a alkyl of 1 to 10 carbon atoms; cycloalkyl of 3 to 10 carbon atoms, aralkyl of 7 to 20 carbon atoms, wherein the aryl group of the aralkyl group of R$_4$ is optionally substituted with alkyl of 1 to 10 carbon atoms, nitro, halogen cyano, —OR$_7$,

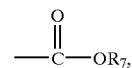

trifluoromethyl or trifluoromethoxy;

R$_5$ is hydrogen; alkyl of 1 to 10 carbon atoms; formyl; alkanoyl of 2 to 7 carbon atoms; alkenoyl of 3 to 7 carbon atoms;

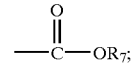

—SO$_2$R$_7$; aroyl of 7 to 12 carbon atoms optionally substituted with one to three substituents each independently selected from the group halogen, cyano, alkyl of 1 to 10 carbon atoms, alkoxy of 1 to 10 carbon atoms, —CF$_3$ and phenyl; arylalkenoyl of 9 to 20 carbon atoms wherein the aryl group is optionally substituted with one to three substituents each independently selected from the group halogen, cyano, alkyl of 1 to 10 carbon atoms, alkoxy of 1 to 10 carbon atoms, CF$_3$, and phenyl and substituted phenyl where the substituents are selected from halogen, cyano, alkyl of 1 to 10 carbon atoms, alkoxy of 1 to 10 carbon atoms and —CF$_3$; arylsulfonyl of 6 to 12 carbon atoms wherein the aryl group is optionally substituted with one to three substituents each independently selected from the group halogen, carboxy, alkyl of 1 to 10 carbon atoms, nitro, amino, alkoxy of 1 to 10 carbon atoms, and alkyl amino of 1 to 10 carbon atoms; arylalkanoyl of 8 to 12 carbon atoms wherein the aryl group is optionally substituted with one to three substituents each independently selected from the group halogen, cyano, alkyl of 1 to 10 carbon atoms, alkoxy of 1 to 10 carbon atoms, $CF_3$, and phenyl and substituted phenyl where the substituents are selected from halogen, cyano, alkyl of 1 to 10 carbon atoms, alkoxy of 1 to 10 carbon atoms and —$CF_3$; or arylalkylsulfonyl of 7 to 12 carbon atoms wherein the aryl group is optionally substituted with one to three substituents each independently selected from the group halogen, carboxy, alkyl of 1 to 10 carbon atoms, nitro, amino, alkoxy of 1 to 10 carbon atoms, and alkyl amino of 1 to 10 carbon atoms;

$R_6$ is alkyl of 1 to 10 carbon atoms; or aryl of 6 to 12 carbon atoms wherein the aryl group is optionally substituted with one to three substituents each independently selected from the group halogen, carboxy, alkyl of 1 to 10 carbon atoms, nitro, amino, alkoxy of 1 to 10 carbon atoms, and alkyl amino of 1 to 10 carbon atoms;

$R_7$ is a alkyl of 1 to 10 carbon atoms optionally substituted with halogen;

Aryl means a homocyclic aromatic radical, whether or not fused, having 6 to 12 carbon atoms optionally substituted with one to three substituents;

Aroyl of 7 to 12 carbon atoms refers to —C(O)aryl; or a pharmaceutically acceptable salt.

6. The method of claim 5 in which the smooth muscle adversely contracting causes urinary incontinence.

7. The method of claim 5 in which the smooth muscle adversely contracting causes irritable bowel syndrome.

* * * * *